United States Patent
Østensen et al.

(10) Patent No.: US 6,375,931 B2
(45) Date of Patent: *Apr. 23, 2002

(54) CONTRAST AGENTS

(75) Inventors: Jonny Østensen; Morten Eriksen, both of Oslo; Sigmund Frigstad, Trondheim; Pål Rongved, Olso, all of (NO)

(73) Assignee: Nycomed Imaging AS, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/291,277

(22) Filed: Apr. 14, 1999

Related U.S. Application Data

(63) Continuation of application No. PCT/GB97/02898, filed on Oct. 21, 1997.
(60) Provisional application No. 60/044,452, filed on Apr. 29, 1997.

(30) Foreign Application Priority Data

Oct. 21, 1996 (GB) .............................................. 9621884
Apr. 23, 1997 (GB) .............................................. 9708239

(51) Int. Cl.[7] ................................................. A61B 8/00
(52) U.S. Cl. ..................................................... 424/9.52
(58) Field of Search .............................. 424/9.52, 9.51, 424/9.5, 450, 455, 489; 600/458, 441

(56) References Cited

U.S. PATENT DOCUMENTS

| | | | |
|---|---|---|---|
| 5,117,830 A | * 6/1992 | McAfee et al. | 424/1.11 |
| 5,512,268 A | * 4/1996 | Grinstaff et al. | 424/9.322 |
| 5,536,489 A | 7/1996 | Lohrmann et al. | 424/9.52 |
| 5,560,364 A | 10/1996 | Porter | 600/458 |
| 5,585,112 A | 12/1996 | Unger et al. | 424/450 |
| 5,639,443 A | * 6/1997 | Schutt et al. | 424/9.52 |
| 5,798,091 A | * 8/1998 | Trevino et al. | 424/9.51 |
| 5,846,517 A | * 12/1998 | Unger | 424/9.52 |
| 6,054,118 A | * 4/2000 | Ostensen | 424/9.52 |

FOREIGN PATENT DOCUMENTS

| | | |
|---|---|---|
| DE | 44 06 474 A | 8/1995 |
| WO | WO 94 16739 A | 8/1994 |
| WO | WO 95 03835 A | 2/1995 |
| WO | WO 96 08234 A | 3/1996 |
| WO | WO 96 26746 A | 9/1996 |
| WO | WO 96 40281 A | 12/1996 |

* cited by examiner

Primary Examiner—Michael G. Hartley
(74) Attorney, Agent, or Firm—Royal N. Ronning, Jr.

(57) ABSTRACT

Ultrasonic visualization of a subject, particularly of perfusion in the myocardium and other tissues, is performed using novel gas-containing contrast agent preparations which promote controllable and temporary growth of the gas phase in vivo following administration and can therefore act as deposited perfusion tracers. The preparations include a coadministerable composition comprising a diffusible component capable of inward diffusion into the dispersed gas phase to promote temporary growth thereof. In cardiac perfusion imaging the preparations may advantageously be coadministered with vasodilator drugs such as adenosine in order to enhance the differences in return signal intensity from normal and hypoperfused myocardial tissue respectively.

32 Claims, No Drawings

CONTRAST AGENTS

This application is a continuation of pending international application number PCT/GB/97/02898 filed Oct. 21, 1997 (of which the entire disclosure of the pending, prior application is hereby incorporated by reference), which itself is a continuation of U.S. provisional application No. 60/044,452 filed Apr. 29, 1997.

This invention relates to ultrasound imaging, more particularly to novel contrast agent preparations and their use in ultrasound imaging, for example in visualising tissue perfusion.

It is well known that contrast agents comprising dispersions of microbubbles of gases are particularly efficient backscatterers of ultrasound by virtue of the low density and ease of compressibility of the microbubbles. Such microbubble dispersions, if appropriately stabilised, may permit highly effective ultrasound visualisation of, for example, the vascular system and tissue microvasculature, often at advantageously low doses.

The use of ultrasonography to measure blood perfusion (i.e. blood flow per unit of tissue mass) is of potential value in, for example, tumour detection, tumour tissue typically having different vascularity from healthy tissue, and studies of the myocardium, e.g. to detect myocardial infarctions. A problem with the application of existing ultrasound contrast agents to cardiac perfusion studies is that the information content of images obtained is degraded by attenuation caused by contrast agent present in the ventricles of the heart.

The present invention is based on the finding that ultrasonic visualisation of a subject, in particular of perfusion in the myocardium and other tissues, may be achieved and/or enhanced by means of gas-containing contrast agent preparations which promote controllable and temporary growth of the gas phase in vivo following administration. Thus, for example, such contrast agent preparations may be used to promote controllable and temporary retention of the gas phase, for example in the form of microbubbles, in tissue microvasculature, thereby enhancing the concentration of gas in such tissue and accordingly enhancing its echogenicity, e.g. relative to the blood pool.

It will be appreciated that such use of gas as a deposited perfusion tracer differs markedly from existing proposals regarding intravenously administrable microbubble ultrasound contrast agents. Thus it is generally thought necessary to avoid microbubble growth since, if uncontrolled, this may lead to potentially hazardous tissue embolisation. Accordingly it may be necessary to limit the dose administered and/or to use gas mixtures with compositions selected so as to minimise bubble growth in vivo by inhibiting inward diffusion of blood gases into the microbubbles (see e.g. WO-A-9503835 and WO-A-9516467).

In accordance with the present invention, on the other hand, a composition comprising a dispersed gas phase is coadministered with a composition comprising at least one substance which has or is capable of generating a gas or vapour pressure in vivo sufficient to promote controllable growth of the said dispersed gas phase through inward diffusion thereto of molecules of gas or vapour derived from said substance, which for brevity is hereinafter referred to as a "diffusible component", although it will be appreciated that transport mechanisms other than diffusion may additionally or alternatively be involved in operation of the invention, as discussed in greater detail hereinafter.

This coadministration of a dispersed gas phase-containing composition and a composition comprising a diffusible component having an appropriate degree of volatility may be contrasted with previous proposals regarding administration of volatile substances alone, e.g. in the form of phase shift colloids as described in WO-A-9416739. Thus the contrast agent preparations of the present invention permit control of factors such as the probability and/or rate of growth of the dispersed gas by selection of appropriate constituents of the coadministered compositions, as described in greater detail hereinafter, whereas administration of the aforementioned phase shift colloids alone may lead to generation of microbubbles which grow uncontrollably and unevenly, possibly to the extent where at least a proportion of the microbubbles may cause potentially dangerous embolisation of, for example, the myocardial vasculature and brain (see e.g. Schwarz, *Advances in Echo-Contrast* [1994(3)], pp. 48–49).

It has also been found that administration of phase shift colloids alone may not lead to reliable or consistent in vivo volatilisation of the dispersed phase to generate gas or vapour microbubbles. Grayburn et al. in *J. Am. Coll. Carding.* 26(5) [1995], pp. 1340–1347 suggest that preactivation of perfluoropentane emulsions may be required to achieve myocardial opacification in dogs at effective imaging doses low enough to avoid haemodynamic side effects. An activation technique for such colloidal dispersions, involving application of hypobaric forces thereto, is described in WO-A-9640282; typically this involves partially filling a syringe with the emulsion and subsequently forcibly withdrawing and then releasing the plunger of the syringe to generate a transient pressure change which causes formation of gas microbubbles within the emulsion. This is an inherently somewhat cumbersome technique which may fail to give consistent levels of activation.

It is stated in U.S. Pat. No. 5,536,489 that emulsions of water-insoluble gas-forming chemicals such as perfluoropentane may be used as contrast agents for site-specific imaging, the emulsions only generating a significant number of image-enhancing gas microbubbles upon application of ultrasonic energy to a specific location in the body which it is desired to image. Our own research has shown that emulsions of volatile compounds such as 2-methylbutane or perfluoropentane give no detectable echo enhancement either in vitro or in vivo when ultrasonicated at energy levels which are sufficient to give pronounced contrast effects using two component contrast agents in accordance with the present invention.

According to one aspect of the invention there is provided a combined preparation for simultaneous, separate or sequential use as a contrast agent in ultrasound imaging, said preparation comprising:

i) an injectable aqueous medium having gas dispersed therein; and ii) a composition comprising a diffusible component capable of diffusion in vivo into said dispersed gas so as at least transiently to increase the size thereof.

According to a further aspect of the invention there is provided a method of generating enhanced images of a human or non-human animal subject which comprises the steps of:

i) injecting a physiologically acceptable aqueous medium having gas dispersed therein into the vascular system of said subject;

ii) before, during or after injection of said aqueous medium administering to said subject a composition comprising a diffusible component capable of diffusion in vivo into said dispersed gas so as at least transiently to increase the size thereof; and iii) generating an ultrasound image of at least a part of said subject.

This method according to the invention may advantageously be employed in visualising tissue perfusion in a subject, the increase in size of the dispersed gas being utilised to effect enrichment or temporary retention of gas in the microvasculature of such tissue, thereby enhancing its echogenicity.

Any biocompatible gas may be present in the gas dispersion, the term "gas" as used herein including any substances (including mixtures) at least partially, e.g. substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, may be particularly advantageous in view of the recognised high stability in the bloodstream of microbubbles containing such gases. Other gases with physicochemical characteristics which cause them to form highly stable microbubbles in the bloodstream may likewise be useful.

The dispersed gas may be administered in any convenient form, for example using any appropriate gas-containing ultrasound contrast agent formulation as the gas-containing composition. Representative examples of such formulations include microbubbles of gas stabilised (e.g. at least partially encapsulated by a coalescence-resistant surface membrane (for example gelatin, e.g. as described in WO-A-8002365), a filmogenic protein (for example an albumin such as human serum albumin, e.g. as described in U.S. Pat. Nos. 4,718, 433, 4,774,958, 4,844,882, EP-A-0359246, WO-A-9112823, WO-A-9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid-polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780, WO-A-9503835 or WO-A-9729783).

Other useful gas-containing contrast agent formulations include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure).

The disclosures of all of the above-described documents relating to gas-containing contrast agent formulations are incorporated herein by reference.

Gas microbubbles and other gas-containing materials such as microparticles preferably have an initial average size not exceeding 10 $\mu$m (e.g. of 7 $\mu$m or less) in order to permit their free passage through the pulmonary system following administration, e.g. by intravenous injection. However, larger microbubbles may be employed where, for example, these contain a mixture of one or more relatively blood-soluble or otherwise diffusible gases such as air, oxygen, nitrogen or carbon dioxide with one or more substantially insoluble and non-diffusible gases such as perflucrocarbons. Outward diffusion of the soluble/diffusible gas content following administration will cause such microbubbles rapidly to shrink to a size which will be determined by the amount of insoluble/non-diffusible gas present and which may be selected to permit passage of the resulting microbubbles through the lung capillaries of the pulmonary system.

Since dispersed gas administered in accordance with the invention is caused to grow in vivo through interaction with diffusible component, the minimum size of the microbubbles, solid-associated gas etc. as administered may be substantially lower than the size normally thought necessary to provide significant interaction with ultrasound (typically ca. 1–5 $\mu$m at conventionally-employed imaging frequencies); the dispersed gas moieties may therefore have sizes as low as, for example, 1 nm or below. The invention may accordingly permit use of gas-containing compositions which have not hitherto been proposed for use as ultrasound contrast agents, e.g. because of the low size of the dispersed gas moieties.

Where phospholipid-containing compositions are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin, semisynthetic (e.g. partially or fully hydrogenated) lecithins and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, for example as described in WO-A-9729783, may be particularly advantageous.

Representative examples of gas-containing microparticulate materials which may be useful in accordance with the invention include carbohydrates (for example hexoses such as glucose, fructose or galactose; disaccharides such as sucrose, lactose or maltose; pentoses such as arabinose, xylose or ribose; $\alpha$-, $\beta$- and $\gamma$-cyclodextrins; polysaccharides such as starch, hydroxyethyl starch, amylose, amylopectin, glycogen, inulin, pulullan, dextran, carboxymethyl dextran, dextran phosphate, ketodextran, amincoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate and meglumine diatrizoate), and polypeptides and proteins (e.g. gelatin or albumin such as human serum albumin).

Other gas-containing materials which may be useful in accordance with the invention include gas-containing material stabilised by metals (e.g. as described in U.S. Pat. Nos. 3,674,461 or 3,528,809) gas-containing material stabilised by synthetic polymers (e.g. as described in U.S. Pat. No. 3,975,194 or by Farnand in *Powder Technology* 22 [1979], pp. 11–16), commercially available microspheres of the Expancel® type, e.g. Expancel 551 DE (see e.g. *Eur. Plast. News* 9(5) [1982], p. 39, *Nonwovens Industry* [1981], p. 21 and *Mat. Plast. Elast.* 10 [1980], p. 468), commercially available microspheres of the Ropaque® type (see e.g. *J. Coatings Technol.* 55(707) [1983], p. 79), micro- and nano-sized gas-containing structures such as zeolites, inorganic or organic aerogels, nanosized open void-containing chemical structures such as fullerenes, clathrates or nanotubes (e.g. as described by G. E. Gadd in *Science* 277 (5328) [1997], pp. 933–936), and natural surfactant-stabilised microbubble dispersions (e.g. as described by d'Arrigo in *"Stable Gas-in-Liquid Emulsions, Studies in physical and theoretical chemistry"* 40—Elsevier, Amsterdam [1986]).

A wide range of diffusible components may be used in accordance with the invention, including gases/vapours, volatile liquids, volatile solids and precursors capable of gas generation, e.g. upon administration, the principal requirement being that the component should either have or be capable of generating a sufficient gas or vapour pressure in vivo (e.g. at least 10 torr) so as to be capable of promoting inward diffusion of gas or vapour molecules into the dispersed gas. It will be appreciated that mixtures of two or more diffusible components may if desired be employed in accordance with the invention; references herein to "the diffusible component" are to be interpreted as including such mixtures. Similarly, references to administration of a diffusible component are intended also to embrace administration of two or more such components, either as mixtures or as plural administrations.

The composition comprising the diffusible component may take any appropriate form and may be administered by any appropriate method, the route of administration depending in part on the area of the subject which is to be investigated. Thus, for example, oral administration of an appropriate composition comprising a diffusible component may be particularly useful where it is desired to promote temporary retention of gas in the tissue of the gastrointestinal wall. In representative embodiments of such applications the gas dispersion may be injected intravenously in doses similar to those used in echocardiography and the diffusible component may be formulated as an orally administrable emulsion, e.g. a perfluorocarbon-in-water emulsion as described in further detail hereinafter, for example being used at a dose of 0.2–1.0 $\mu$l perfluorocarbon/kg. Following administration and distribution of the two compositions, growth of the gas dispersion in the capillary blood pool in the gastric or intestinal wall may enhance contour contrast from these regions. It will be appreciated that the reverse combination of an orally administrable gas dispersion and intravenously injectable diffusible component may be useful in providing contour contrast from the inner wall or mucosa of the gastrointestinal system.

It may be advantageous when using such orally administrable gas dispersion or diffusible component compositions to incorporate chemical groups or substances which promote adhesion to the wall of the gastrointestinal tract, for example by admixture with the composition or by attachment to a component thereof, e.g. a surfactant or other stabilising moiety, since this may stimulate growth of the dispersed gas phase by enhancing its contact with the diffusible component. Examples of such adhesion-promoting groups/substances have previously been described in relation to, for example, gastrointestinal X-ray contrast agents, and include acrylic esters as described in WO-A-9722365, iodophenol sulphonate esters as described in U.S. Pat. No. 5,468,466 and iodinated phenyl esters as described in U.S. Pat. No. 5,260,049.

Inhalation of a suitably volatile diffusible component may, for example, be used to promote growth of the administered gas dispersion immediately following its passage through the lung capillaries, e.g. so that the gas then becomes temporarily retained in the capillaries of the myocardium. In such embodiments growth of the dispersed gas may be further increased by raising the lung pressure of the diffusible component, e.g. by an excess of up to 0.5 bar, for example by using a respirator or by having the subject exhale against a resistance.

Intramuscular or subcutaneous injection of appropriately formulated diffusible component compositions, e.g. incorporating a physiologically acceptable carrier liquid, may, for example, advantageously be employed where it is desired specifically to limit the effect of the component to a particular target area of the subject. One example of a composition for subcutaneous injection comprises nanoparticles such as are used for lymph angiography. Subcutaneously injected diffusible component may be taken up by the lymph system, where it may cause growth of an intravenously injected gas dispersion, thereby facilitating imaging of lymph nodes. The reverse combination of a subcutaneously injected gas diapersion and intravenously injected diffusible component may similarly be employed.

Intravenous injection of appropriately formulated diffusible component compositions, e.g. incorporating a physiologically acceptable carrier liquid, permits considerable versatility in operation of the invention since, as discussed in greater detail hereinafter, the constituents of the gas dispersion and diffusible component compositions may be selected to control parameters such as the onset and rate of growth of the dispersed gas and thus the parts of the body in which tissue echogenicity may be enhanced by temporary retention of gas, for example in the microvasculature thereof.

Appropriate topical formulations may be applied cutaneously so as to promote transcutaneous absorption of the diffusible component. Such administration may have applications in imaging and/or therapy of the skin, subcutis and adjacent regions and organs, for example in targeting the peripheral circulation of body extremities such as legs.

Diffusible components for administration orally or by injection may, for example, be formulated as solutions in or mixtures with water and/or one or more water-miscible and physiologically acceptable organic solvents, such as ethanol, glycerol or polyethylene glycol; dispersions in an aqueous medium, for example as the oil phase or a constituent of the oil phase of an oil-in-water emulsion; microemulsions, i.e. systems in which the substance is effectively dissolved in the hydrophobic interiors of surfactant micelles present in an aqueous medium; or in association with microparticles or nanoparticles dispersed in an appropriate carrier liquid, for example being adsorbed on microparticle or nanoparticle surfaces and/or contained within voids, cavities or pores of microparticles or nanoparticles, or encapsulated within microcapsules.

Where a diffusible component is to be administered as a solution, the partial pressure derived therefrom in vivo will depend on the concentration of the component, e.g. in the blood stream, and the corresponding pressure of pure component material, for example in accordance with Raoult's law in a system approaching ideality. Thus if the component has low water solubility it is desirable that it should have a sufficient vapour pressure in pure form at normal body temperature, e.g. at least 50 torr, preferably at least 100 torr. Examples of relatively water-insoluble components with high vapour pressures include gases such as those listed hereinbefore as possible microbubble gases.

Representative examples of more highly water-soluble/water-miscible diffusible components, which may therefore exhibit lower vapour pressures at body temperature, include aliphatic ethers such as ethyl methyl ether or methyl propyl ether; aliphatic esters such as methyl acetate, methyl formate or ethyl formate; aliphatic ketones such as acetone; aliphatic amides such as N,N-dimethylformamide or N,N-dimethylacetamide; and aliphatic nitriles such as acetonitrile.

It may, however, be preferred to employ a substantially water-immiscible diffusible component formulated as an emulsion (i.e. a stabilised suspension) in an appropriate aqueous medium, since in such systems the vapour pressure in the aqueous phase of the diffusible component will be substantially equal to that of pure component material, even in very dilute emulsions. In such embodiments the diffusible component may, for example, be formulated as part of a proprietary registered pharmaceutical emulsion, such as Intralipid® (Pharmacia).

The diffusible component in such emulsions is advantageously a liquid at processing and storage temperature, which may for example be as low as −10° C. if the aqueous phase contains appropriate antifreeze material, while being a gas or exhibiting a substantial vapour pressure at body temperature. Appropriate compounds may, for example, be selected from the various lists of emulsifiable low boiling liquids given in the aforementioned WO-A-9416379, the contents of which are incorporated herein by reference. Specific examples of emulsifiable diffusible components include aliphatic ethers such as diethyl ether; polycyclic oils or alcohols such as menthol, camphor or eucalyptol; heterocyclic compounds such as furan or dioxane; aliphatic hydrocarbons, which may be saturated or unsaturated and straight chained or branched, e.g. as in n-butane, n-pentane, 2-methylpropane, 2-methylbutane, 2,2-dimethylpropane, 2,2-dimethylbutane, 2,3-dimethylbutane, 1-butene, 2-butene, 2-methylpropene, 1,2-butadiene, 1,3-butadiene, 2-methyl-1-butene, 2-methyl-2-butene, isoprene, 1-pentene, 1,3-pentadiene, 1,4-pentadiene, butenyne, 1-butyne, 2-butyne or 1,3-butadiyne; cycloaliphatic hydrocarbons such as cyclobutane, cyclobutene, methylcyclopropane or cyclopentane; and halogenated low molecular weight hydrocarbons (e.g. containing up to 7 carbon atoms). Representative halogenated hydrocarbons include dichloromethane, methyl bromide, 1,2-dichloroethylene, 1,1-dichloroethane, 1-bromoethylene, 1-chloroethylene, ethyl bromide, ethyl chloride, 1-chloropropene, 3-chloropropene, 1-chloropropane, 2-chloropropane and t-butyl chloride. Advantageously at least some of the halogen atoms are fluorine atoms, for example as in dichlorofluoromethane, trichlorofluoromethane, 1,2-dichloro-1,2-difluoroethane, 1,2-dichloro-1,1,2,2-tetrafluoroethane, 1,1,2-trichloro-1,2,2-trifluoroethane, 2-bromo-2-chloro-1,1,1-trifluoroethane, 2-chloro-1,1,2-trifluoroethyl difluoromethyl ether, 1-chloro-2,2,2-trifluoroethyl difluoromethyl ether, partially fluorinated alkanes (e.g. pentafluoropropanes such as 1H,1H,3H-pentafluoropropane, hexafluorobutanes, nonafluorobutanes such as 2H-nonafluoro-t-butane, and decafluoropentanes such as 2H,3H-decafluoropentane), partially fluorinated alkenes (e.g. heptafluoropentenes such as 1H,1H,2H-heptafluoropent-1-ene, and nonafluorohexenes such as 1H,1H,2H-nonafluorohex-1-ene), fluorinated ethers (e.g. 2,2,3,3,3-pentafluoropropyl methyl ether or 2,2,3,3,3-pentafluoropropyl difluoromethyl ether) and, more preferably, perfluorocarbons. Examples of perfluorocarbons include perfluoroalkanes such as perfluorobutanes, perfluoropentanes, perfluorohexanes (e.g. perfluoro-2-methylpentane), perfluoroheptanes, perfluorooctanes, perfluorononanes and perfluorodecanes; perfluorocycloalkanes such as perfluorocyclobutane, perfluorodimethylcyclobutanes, perfluorocyclopentane and perfluoromethylcyclopentane; perfluoroalkenes such as perfluorobutenes (e.g. perfluorobut-2-ene or perfluorobuta-1,3-diene), perfluoropentenes (e.g. perfluoropent-1-ene) and perfluorohexenes (e.g. perfluoro-2-methylpent-2-ene or perfluoro-4-methylpent-2-ene); perfluorocycloalkenes such as perfluorocyclopentene or perfluorocyclopentadiene; and perfluorinated alcohols such as perfluoro-t-butanol.

Such emulsions may also contain at least one surfactant in order to stabilise the dispersion; this may be the same as or different from any surfactant(s) used to stabilise the gas dispersion. The nature of any such surfactant may significantly affect factors such as the rate of growth of the dispersed gas phase. In general a wide range of surfactants may be useful, for example selected from the extensive lists given in EP-A-0727225, the contents of which are incorporated herein by reference. Representative examples of useful surfactants include fatty acids (e.g. straight chain saturated or unsaturated fatty acids, for example containing 10–20 carbon atoms) and carbohydrate and triglyceride esters thereof, phospholipids (e.g. lecithin), fluorine-containing phospholipids, proteins (e.g. albumins such as human serum albumin), polyethylene glycols, and block copolymer surfactants (e.g. polyoxyethylene-polyoxypropylene block copolymers such as Pluronics, extended polymers such as acyloxyacyl polyethylene glycols, for example polyethyleneglycol methyl ether 16-hexadecanoyloxy-hexadecanoate, e.g. wherein the polyethylene glycol moiety has a molecular weight of 2300, 5000 or 10000), and fluorine-containing surfactants (e.g. as marketed under the trade names Zonyl and Fluorad, or as described in WO-A-9639197, the contents of which are incorporated herein by reference). Particularly useful surfactants include phospholipids comprising molecules with net overall negative charge, such as naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins.

The droplet size of the dispersed diffusible component in emulsions intended for intravenous injection should preferably be less than 10 $\mu$m, e.g. less than 7 $\mu$m, and greater than 0.1 $\mu$m in order to facilitate unimpeded passage through the pulmonary system.

As noted above, water-immiscible diffusible components may also be formulated as microemulsions. Such systems are advantageous by virtue of their thermodynamic stability and the fact that the diffusible component is in practice uniformly distributed throughout the aqueous phase; microemulsions therefore have the appearance of solutions but may exhibit the properties of emulsions as regards the partial pressure of the dispersed phase.

Gas precursors which may be used include any biocompatible components capable of gas generation in vivo, i.e. at body temperature and physiological pH. Representative examples include inorganic and organic carbonates and bicarbonates, and nitrogen-generating substances such as pyrazolines, pyrazoles, triazolines, diazoketones, diazonium salts, tetrazoles and azides. It will be appreciated that in such systems it is the ultimately generated gas which is the actual diffusible component.

In order to ensure maximum volatilisation of the diffusible component following administration and to enhance growth of the dispersed gas, both of which are endothermic processes, it may be advantageous to manipulate the temperature of the solution or suspension of the diffusible component and/or the gas dispersion prior to administration and/or to incorporate exothermically reactive constituents therein; the use of such constituents which react exothermically under the influence of ultrasound radiation may be particularly advantageous.

Growth of the dispersed gas phase in vivo may, for example, be accompanied by expansion of any encapsulating material (where this has sufficient flexibility) and/or by abstraction of excess surfactant from the administered material to the growing gas-liquid interfaces. It is also possible, however, that stretching of the encapsulating material and/or interaction of the material with ultrasound may substantially increase its porosity. Whereas such disruption of encapsulating material has hitherto in many cases been found to lead to rapid loss of echogenicity through outward diffusion and dissolution of the gas thereby exposed, we have found that when using contrast agent preparations in accordance with the present invention, the exposed gas exhibits substantially stability. Whilst not wishing to be bound by theoretical calculations, we believe that the exposed gas, e.g. in the form of liberated microbubbles, may be stabilised, e.g. against collapse of the microbubbles, by the supersaturated environment generated by the diffusible component, which provides an inward pressure gradient to counteract the outward diffusive tendency of the microbubble gas. The exposed gas surface, by virtue of the substantial absence of encapsulating material, may cause the contrast agent preparation to exhibit exceptionally favourable acoustic properties as evidenced by high backscatter and low energy absorption (e.g. as expressed by high backscatter: attenuation ratios); this echogenic effect may continue for a significant period, even during continuing ultrasound irradiation.

The stabilising effect of coadministered diffusible component may therefore be used to great advantage to enhance both the duration and magnitude of the echogenicity of existing gas-containing contrast agent formulations in cases where these parameters may be insufficient when the contrast agent composition is administered alone. Thus, for example, the duration of effect of albumin-based contrast agents is often severely limited by collapse of the encapsulating albumin material, either as a result of systolic pressure changes in the heart or venous system or as a consequence of ultrasound irradiation, but may be substantially enhanced by coadministration with a diffusible component in accordance with the present invention.

In a representative embodiment of the method of the invention a composition comprising a gas dispersion and a composition comprising a diffusible component suspension are selected such that at least a proportion of the dispersed gas passes through the lungs and then undergoes rapid growth following passage from the lungs through inward diffusion of the diffusible component, so as temporarily to be retained in the myocardium and thereby permit ultrasonic visualisation of myocardial perfusion. As the concentration of volatile diffusible component in the bloodstream falls away, e.g. as the component is cleared from the blood, for example by removal through the lungs and exhalation by the subject, by metabolism or by redistribution to other tissues, the diffusible component will typically diffuse out of the dispersed gas, which will therefore shrink towards its initial smaller size, and ultimately once more becoming free flowing in the bloodstream, typically being removed therefrom by the reticuloendothelial system. This pattern of a substantial transient increase in echogenicity followed by disappearance of contrast effect is markedly different from any echogenic properties exhibited by either of the two compositions when administered alone. It will be appreciated from the foregoing that control of the duration of retention of the dispersed gas may therefore be achieved by appropriate adjustment of the dose and/or formulation of the diffusible component.

Other capillary systems, such as but not limited to those of the kidney, liver, spleen, thyroid, skeletal muscle, breast and penis, may similarly be imaged.

It will be appreciated that factors such as the rate and/or extent of growth of the dispersed gas may in general be controlled by appropriates selection of the gas and any encapsulating stabilising material and, more particularly, the nature of the diffusible component and the manner in which it is formulated, including the nature of any surfactant employed and the size of the dispersed phase droplets where the component is formulated as an emulsion; in this last context, for a given amount of emulsified diffusible component, a reduction in droplet size may enhance the rate of transfer of diffusible component relative to that from larger droplets since more rapid release may occur from smaller droplets having higher surface area:volume ratios. Other parameters permitting control include the relative amounts in which the two compositions are administered and, where these are administered separately, the order of administration, the time interval between the two administrations, and possible spatial separation of the two administrations. In this last respect it will be appreciated that the inherent diffusivity of the diffusible component may permit its application to different parts of the body in a wide variety of ways, for example by inhalation, cutaneously, subcutaneously, intravenously, intramuscularly or orally, whereas the available forms of administration for the dispersed gas may be somewhat more limited.

Particularly important parameters with regard to the diffusible component are its solubility in water/blood and its diffusibility (e.g. as expressed by its diffusion constants), which will determine its rate of transport through the carrier liquid or blood, and its permeability through any membrane encapsulating the dispersed gas. The pressure generated by the diffusible component in vivo will also affects its rate of diffusion into the dispersed gas, as will its concentration. Thus, in accordance with Fick's law, the concentration gradient of diffusible component relative to the distance between, for example, individual gas microbubbles and emulsion droplets, together with the diffusion coefficient of the diffusible substance in the surrounding liquid medium, will determine the rate of transfer by simple diffusion; the concentration gradient is determined by the solubility of the diffusible component in the surrounding medium and the distance between individual gas microbubbles and emulsion droplets.

The effective rate of transport of the diffusible component may, if desired, be controlled by adjusting the viscosity of the dispersed gas phase composition and/or the diffusible component composition, for example by incorporating one or more biocompatible viscosity enhancers such as X-ray contrast agents, polyethylene glycols, carbohydrates, proteins, polymers or alcohols into the formulation. It may, for example, be advantageous to coinject the two compositions as a relatively high volume bolus (e.g. having a volume of at least 20 ml in the case of a 70 kg human subject), since this will delay complete mixing of the constituents with blood (and thus the onset of growth of the dispersed gas) until after entry into the right ventricle of the heart and the lung capillaries. The delay in growth of the dispersed gas may be maximised by employing carrier liquid which is undersaturated with respect to gases and any other diffusible components as hereinbefore defined, e.g. as a result of being cooled.

As noted above, transport mechanisms other than diffusion may be involved in operation of the invention. Thus, for example, transport may also occur through hydrodynamic flow within the surrounding liquid medium; this may be important in vessels and capillaries where high shear rate flow may occur. Transport of diffusible component to the dispersed gas may also occur as a result of collision or near-collision processes, e.g. between gas microbubbles and emulsion droplets, for example leading to adsorption of diffusible component at the microbubble surface and/or penetration of diffusible component into the microbubble, i.e. a form of coalescence. In such cases the diffusion coefficient and solubility of the diffusible component have a minimal effect on the rate of transfer, the particle size of the diffusible component (e.g. the droplet size where this is formulated as an emulsion) and the collision frequency between microbubbles and droplets being the principal factors controlling the rate and extent of microbubble growth. Thus, for example, for a given amount of emulsified diffusible component, a reduction in droplet size will lead to an increased overall number of droplets and so may enhance the rate of transfer by reducing the mean interparticle distance between the gas microbubbles and emulsion droplets and thus increasing the probability of collision and/or coalescence. It will be appreciated that the rate of transfers proceeding through collision processes may be markedly enhanced if additional oscillatory movement is imparted to the gas microbubbles and emulsion droplets of the diffusible component through application of ultrasonic energy. The kinetics of collision processes induced by such ultrasonic energy may differ from the kinetics for transport of diffusible component in carrier liquid and/or blood, for example in that specific energy levels may be necessary to initiate coalescence of colliding gas microbubbles and emulsion droplets. Accordingly it may be advantageous to select the size and therefore the mass of the emulsion droplets so that they generate sufficient collisional force with the oscillating microbubbles to induce coalescence.

As also noted above, the permeability of any material encapsulating the dispersed gas phase is a parameter which may affect the rate of growth of the gas phase, and it may therefore be desirable to select a diffusible component which readily permeates any such encapsulating material (which may, for example, be a polymer or surfactant membrane, e.g. a monolayer or one or more bilayers of a membrane-forming surfactant such as a phospholipid). We have found, however, that substantially impermeable encapsulating material may also be used, since it appears that sonication, including sonication at lower and higher frequencies than normally used in medical ultrasound imaging (e.g. in the range 10 Hz to 1 GHz, preferably between 1 kHz and 10 MHz) and with either continuous radiation or simple or complex pulse patterns, of combined contrast agent preparations administered according to the invention may itself promote or enhance growth of the dispersed gas. Such growth may, for example, be induced by the ultrasound irradiation used to effect an investigation or by preliminary localised irradiation, e.g. serving to effect temporary retention of gas in the microvasculature of a particular target organ. Alternatively, activation of growth of the dispersed gas may be induced by aplication of sufficient amounts of other forms of energy, for example shaking, vibration, an electric field, radiation or particle bombardment, e.g. with neutral particles, ions or electrons.

Whilst we do not wish to be bound by theoretical considerations it may be that ultrasonication at least transiently modifies the permeability of the encapsulating material, the diffusibility of the diffusible component in the surrounding liquid phase and/or the frequency of collisions between emulsion droplets and the encapsulated microbubbles. Since the effect may be observed using extremely short ultrasound pulses (e.g. with durations of ca. 0.3 $\mu$s in B-mode imaging or ca. 2 $\mu$s in Doppler or second harmonic imaging) it seems unlikely to be an example of rectified diffusion, in which ongoing ultrasound irradiation produces a steady increase in the equilibrium radii of gas bubbles (see Leighton, E. G.—"*The Acoustic Bubble*", Academic Press [1994], p. 379), and it may be that the ultrasound pulses disrupt the encapsulating membrane and so enhance growth of the dispersed gas through inward diffusion of diffusible component into the thus-exposed gas phase.

If desired, either the dispersed gas or the diffusible component may comprise an azeotropic mixture or may be selected so that an azeotropic mixture is formed in vivo as the diffusible component mixes with the dispersed gas. Such azeotrope formation may, for example, be used effectively to enhance the volatility of relatively high molecular weight compounds, e.g. halogenated hydrocarbons such as fluorocarbons (including perfluorocarbons) which under standard conditions are liquid at the normal human body temperature of 37° C., such that they may be administered in gaseous form at this temperature. This has substantial benefits as regards the effective echogenic lifetime in vivo of contrast agents containing such azeotropic mixtures since it is known that parameters such as the water solubility, fat solubility, diffusibility and pressure resistivity of compounds such as fluorocarbons decrease with increasing molecular weight.

In general, the recognised natural resistance of azeotropic mixtures to separation of their constituents will enhance the stability of contrast agent components containing the same, both during preparation, storage and handling and following administration.

Azeotropic mixtures useful in accordance with the invention may, for example, be selected by reference to literature relating to azeotropes, by experimental investigation and/or by theoretical predictions, e.g. as described by Tanaka in *Fluid Phase Equilibria* 24 (1985), pp. 187–203, by Kittel, C. and Kroemer, H. in Chapter 10 of *Thermal Physics* (W.H. Freeman & Co., New York, USA, 1980) or by Hemmer, P. C. in Chapters 16–22 of *Statistisk Mekanikk* (Tapir, Trondheim, Norway, 1970), the contents of which are incorporated herein by reference.

One literature example of an azeotrope which effectively reduces the boiling point of the higher molecular weight component to below normal body temperature is the 57:43 w/w mixture of 1,1,2-trichloro-1,2,2-trifluoromethane (b.p. 47.6° C.) and 1,2-difluoromethane (b.p. 29.6° C.) described in U.S. Pat. No. 4,055,049 as having an azeotropic boiling point of 24.9° C. Other examples of halocarbon-containing azeotropic mixtures are disclosed in EP-A-0783017, U.S. Pat. Nos. 5,599,783, 5,605,647, 5,605,882, 5,607,616, 5,607,912, 5,611,210, 5,614,565 and 5,616,821, the contents of which are incorporated herein by reference.

Simons et al. in *J. Chem. Phys.* 18(3) (1950), pp. 335–346 report that mixtures of perfluoro-n-pentane (b.p. 29° C.) and n-pentane (b.p. 36° C.) exhibit a large positive deviation from Raoult's law; the effect is most pronounced for approximately equimolar mixtures. In practice the boiling point of the azeotropic mixture has been found to be about 22° C. or less. Mixtures of perfluorocarbons and unsubstituted hydrocarbons may in general exhibit useful azeotropic properties; strong azeotropic effects have been observed for mixtures of such components having substantially similar boiling points. Examples of other perfluorocarbon:hydrocarbon azeotropes include mixtures of perfluoro-n-hexane (b.p. 59° C.) and n-pentane, where the azeotrope has a boiling point between room temperature and 35° C., and of perfluoro-4-methylpent-2-ene (b.p. 49° C.) and n-pentane, where the azeotrope has a boiling point of approximately 25° C.

Other potentially useful azeotropic mixtures include mixtures of halothane and diethyl ether and mixtures of two or more fluorinated gases, for example perfluoropropane and fluoroethane, perfluoropropane and 1,1,1-trifluoroethane, or perfluoroethane and difluoromethane.

It is known that fluorinated gases such as perfluoroethane may form azeotropes with carbon dioxide (see e.g. WO-A-9502652). Accordingly, administration of contrast agents containing such gases may lead to in vivo formation of ternary or higher azeotropes with blood gases such as carbon dioxide, thereby further enhancing the stability of the dispersed gas.

Where the two compositions of combined contrast agent preparations according to the invention are to be administered simultaneously they may, for example, be injected from separate syringes via suitable coupling means or may be premixed, preferably under controlled conditions such that premature microbubble growth is avoided.

Compositions intended for mixing prior to simultaneous administration may advantageously be stored in appropriate dual or multi-chamber devices. Thus, for example, the gas dispersion composition or a dried precursor therefor [e.g. comprising a lyophilised residue of a suspension of gas microbubbles in an amphiphilic material-containing aqueous medium, particularly wherein the amphiphilic material consists essentially of phospholipid predominantly (e.g. at least 75%, preferably substantially completely) comprising molecules which individually have an overall net (e.g. negative) charge] may be contained in a first chamber such as a vial, to which a syringe containing the diffusible component composition is sealing connected; the syringe outlet is closed, e.g. with a membrane or plug, to avoid premature mixing. Operation of the syringe plunger ruptures the membrane and causes the diffusible component composition to mix with the gas dispersion component or to mix with and reconstitute a precursor therefor; following any necessary or desired shaking and/or dilution, the mixture may be withdrawn (e.g. by syringe) and administered.

Alternatively the two compositions may be stored within a single sealed vial or syringe, being separated by, for example, a membrane or plug; an overpressure of gas or vapour may be applied to either or both compositions. Rupture of the membrane or plug, e.g. by insertion of a hypodermic needle into the vial, leads to mixing of the compositions; this may if desired be enhanced by hand-shaking, whereafter the mixture may be withdrawn and administered. Other embodiments, for example in which a vial containing a dried precursor for the gas dispersion composition is fitted with a first syringe containing a redispersion fluid for said precursor and a second syringe containing the diffusible component composition, or in which a vial containing membrane-separated diffusible component composition and dried precursor for the gas dispersion composition is fitted with a syringe containing redispersion fluid for the latter, may similarly be used.

In embodiments of the invention in which the gas dispersion composition and diffusible component composition are mixed prior to administration, either at the manufacturing stage or subsequently, the mixture will typically be stored at elevated pressure or reduced temperature such that the pressure of the diffusible component is insufficient to provide growth of the dispersed gas. Activation of growth of the dispersed gas may be induced simply by release of excess pressure or by the heating to body temperature which will follow administration of the mixture, or it may if desired be brought about by preheating the mixture immediately before administration.

In embodiments of the invention in which the gas dispersion composition and diffusible component composition are administered separately, the timing between the two administrations may be used to influence the area of the body in which growth of the dispersed gas phase predominantly occurs. Thus, for example, the diffusible component may be injected first and allowed to concentrate in the liver, thereby enhancing imaging of that organ upon subsequent injection of the gas dispersion. Where the stability of the gas dispersion permits, this may likewise be injected first and allowed to concentrate in the liver, with the diffusible component then being administered to enhance the echogenicity thereof.

Imaging modalities which may be used in accordance with the invention include two- and three-dimensional imaging techniques such as B-mode imaging (for example using the time-varying amplitude of the signal envelope generated from the fundamental frequency of the emitted ultrasound pulse, from sub-harmonics or higher harmonics thereof or from sum or difference frequencies derived from the emitted pulse and such harmonics, images generated from the fundamental frequency or the second harmonic thereof being preferred), colour Doppler imaging, Doppler amplitude imaging and combinations of these last two techniques with any of the other modalities described above. For a given dose of the gas dispersion and diffusible component compositions, the use of colour Doppler imaging ultrasound to induce growth of the dispersed gas has been found to give stronger contrast effects during subsequent B-mode imaging, possibly as a result of the higher ultrasound intensities employed. To reduce the effects of movement, successive images of tissues such as the heart or kidney may be collected with the aid of suitable synchronisation techniques (e.g. gating to the ECG or respiratory movement of the subject). Measurement of changes in resonance frequency or frequency absorption which accompany growth of the dispersed gas may also usefully be made to detect the contrast agent.

It will be appreciated that the dispersed gas content of combined contrast agent preparations according to the invention will tend to be temporarily retained in tissue in concentrations proportional to the regional rate of tissue perfusion. Accordingly, when using ultrasound imaging modalities such as conventional or harmonic B-mode imaging where the display is derived directly from return signal intensities, images of such tissue may be interpreted as perfusion maps in which the displayed signal intensity is a function of local perfusion. This is in contrast to images obtained using free-flowing contrast agents, where the regional concentration of contrast agent and corresponding return signal intensity depend on the actual blood content rather than the rate of perfusion of local tissue.

In cardiac studies, where perfusion maps are derived from return signal intensities in accordance with this embodiment of the invention, it may be advantageous to subject a patient to physical or pharmacological stress in order to enhance the distinction, and thus the difference in image intensities, between normally perfused myocardium and any myocardial regions supplied by stenotic arteries. As is known from radionucleide cardiac imaging, such stress induces vasodilatation and increased blood flow in healthy myocardial tissue, whereas blood flow in underperfused tissue supplied by a stenotic artery is substantially unchanged since the capacity for arteriolar vasodilatation is already exhausted by inherent autoregulation seeking to increase the restricted blood flow.

The application of stress as physical exercise or pharmacologically by administration of adrenergic agonists may cause discomfort such as chest pains in patient groups potentially suffering from heart disease, and it is therefore preferable to enhance the perfusion of healthy tissue by administration of a vasodilating drug, for example selected from adenosine, dipyridamole, nitroglycerine, isosorbide mononitrate, prazosin, doxazosin, dihydralazine, hydralazine, sodium nitroprusside, pentoxyphylline, amelodipine, felodipine, isradipine, nifedipine, nimodipine, verapamil, diltiazem and nitrous oxide. In the case of adenosine this may lead to in excess of fourfold increases in coronary blood flow in healthy myocardial tissue, greatly increasing the uptake and temporary retention of contrast agents in accordance with the invention and thus significantly increasing the difference in return signal intensities between normal and hypoperfused myocardial tissue. Because an essentially physical entrapment process is involved, retention of contrast agents according to the invention is highly efficient; this may be compared to the uptake of radionucleide tracers such as thallium 201 and technetium sestamibi, which is limited by low contact time between tracer and tissue and so may require maintenance of vasodilatation for the whole period of blood pool distribution for the tracer (e.g. 4–6 minutes for thallium scintigraphy) to ensure optimum effect. The contrast agents of the invention, on the other hand, do not suffer such diffusion or transport limitations, and since their retention in myocardial tissue may also rapidly be terminated, for example by cessation of growth-generating ultrasound irradiation, the period of vasodilatation needed to achieve cardiac perfusion imaging in accordance with this embodiment of the invention may be very short, for example less than one minute. This will reduce the duration of any possible discomfort caused to patients by administration of vasodilator drugs.

In view of the fact that the required vasodilatation need only be short lasting, adenosine is a particularly useful vasodilating drug, being both an endogenous substance and having a very short-lasting action as evidenced by a blood pool half-life of only 2 seconds. Vasodilatation will accordingly be most intense in the heart, since the drug will tend to reach more distal tissues in less than pharmacologically active concentrations. It will be appreciated that because of this short half-life, repeated injection or infusion of adenosine may be necessary during cardiac imaging in accordance with this embodiment of the invention; by way of example, an initial administration of 150 $\mu$g/kg of adenosine may be made substantially simultaneously with administration of the contrast agent composition, followed 10 seconds later by slow injection of a further 150 $\mu$g/kg of adenosine, e.g. over a period of 20 seconds.

Contrast agent preparations in accordance with the invention may advantageously be employed as delivery agents for bioactive moieties such as therapeutic drugs (i.e. agents having a beneficial effect on a specific disease in a living human or non-human animal), particularly to targeted sites. Thus, for example, therapeutic compounds may be present in the dispersed gas, may be linked to part of an encapsulating wall or matrix, e.g. through covalent or ionic bonds, if desired through a spacer arm, or may be physically mixed into such encapsulating or matrix material; this last option is particularly applicable where the therapeutic compound and encapsulating or matrix material have similar polarities or solubilities.

The controllable growth properties of the dispersed gas may be utilised to bring about its temporary retention in the microvasculature of a target region of interest; use of ultrasonic irradiation to induce growth and thus retention of the gas and associated therapeutic compound in a target structure is particularly advantageous. Localised injection of the gas dispersion composition or, more preferably, the diffusible component composition, e.g. as hereinbefore described, may also be used to concentrate growth of the dispersed gas in a target area.

The therapeutic compound, which may if desired be coupled to a site-specific vector having affinity for specific cells, structures or pathological sites, may be released as a result of, for example, stretching or fracture of the encapsulating or matrix material caused by growth of the dispersed gas, solubilisation of the encapsulating or matrix material, or disintegration of microbubbles or microparticles (e.g. induced by ultra-sonication or by a reversal of the concentration gradient of the diffusible component in the target area). Where a therapeutic agent is chemically linked to an encapsulating wall or matrix, the linkage or any spacer arm associated therewith may advantageously contain one or more labile groups which are cleavable to release the agent. Representative cleavable groups include amide, imide, imine, ester, anhydride, acetal, carbamate, carbonate, carbonate ester and disulphide groups which are biodegradable in vivo, e.g. as a result or hydrolytic and/or enzymatic action.

Representative and non-limiting examples of drugs useful in accordance with this embodiment of the invention include antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, interferon a-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; anticoagulation agents such as warfarin, phenprocoumon or heparin; antithrombotic agents; circulatory drugs such as propranolol; metabolic potentiators such as glutathione; antituberculars such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof; and radiochemicals, e.g. comprising beta-emitters. Of particular importance are antithrombotic agents such as vitamin K antagonists, heparin and agents with heparin-like activity such as antithrombin III, dalteparin and enoxaparin; blood platelet aggregation inhibitors such as ticlopidine, aspirin, dipyridamolea, iloprost and abciximab; and thrombolytic enzymes such as streptokinase and plasminogen activator. Other examples of therapeutics include genetic material such as nucleic acids, RNA, and DNA of natural or synthetic origin, including recombinant RNA and DNA. DNA encoding certain proteins may be used in the treatment of many different types of diseases. For example, tumour necrosis factor or interleukin-2 may be provided to treat advanced cancers; thymidine kinase may be provided to treat ovarian cancer or brain tumors; interleukin-2 may be provided to treat neuroblastoma, malignant melanoma or kidney cancer; and interleukin-4 may be provided to treat cancer.

Contrast agent preparations in accordance with the invention may be used as vehicles for contrast-enhancing moieties for imaging modalities other than ultrasound, for example X-ray, light imaging, magnetic resonance and, more preferably, scintigraphic imaging agents. Controlled growth of the dispersed gas phase may be used to position such agents in areas of interest within the bodies of subjects, for example using ultrasound irradiation of a target organ or tissue to induce the desired controlled growth and temporary retention of the agent, which may then be imaged using the appropriate non-ultrasound imaging modality.

Contrast agent preparations in accordance with the invention may also be used as vehicles for therapeutically active substances which do not necessarily require release from the preparation in order to exhibit their therapeutic affect. Such preparations may, for example, incorporate radioactive atoms or ions such as beta-emitters which exhibit a localised radiation-emitting effect following growth of the dispersed gas phase and temporary retention of the agent at a terget site. It will be appreciated that such agents should preferably be designed so that subsequent shrinkage and cessation of retention of the dispersed gas does not occur until the desired therapeutic radiation dosage has been administered.

Contrast agent preparations in accordance with the invention may additionally exhibit therapeutic properties in their own right. Thus, for example, the dispersed gas may be targeted to capillaries leading to tumours and may act as cell toxic agents by blocking such capillaries. Thus it is possible by applying localised ultrasonic energy to obtain a controlled and localised embolism; this may be of importance as such or in combination with other therapeutic measures. Concentrations of dispersed gas in capillaries may also enhance absorption of ultrasonic energy in hyperthermic therapy; this may be used in, for example, treatment of liver tumours. Irradiation with a relatively high energy (e.g. 5 W) focused ultrasound beam, e.g. at 1.5 MHz, may be appropriate in such applications.

It will be appreciated that the present invention extends to preparations comprising an aqueous medium having gas dispersed therein and a composition comprising a diffusible component as general compositions of matter and to their use for non-imaging agent purposes.

The following non-limitative Examples serve to illustrate the invention.

EXAMPLE 1

Preparations a) Perfluorobutane Gas Dispersion

Hydrogenated phosphatidylserine (100 mg) in a 2% solution of propylene glycol in purified water (20 ml) was heated to 80° C. for 5 minutes and the resulting dispersion was allowed to cool to room temperature overnight. 1 ml portions were transferred to 2 ml vials, the headspace above each portion was flushed with perfluorobutane gas, and the vials were shaken for 45 seconds using an Espe CapMix® mixer for dental materials, yielding milky white microbubble dispersions with a volume median diameter of 5.0 µm, measured using a Coulter Counter (all Coulter Counter measurements were made at room temperature using an instrument fitted with a 50 µm aperture and having a measuring range 1–30 µm; Isoton II was used as electrolyte).

b) Dispersion of Lyophilised Perfluorobutane Gas Dispersion

A sample of the milky white dispersion from Example 1(a) was washed three times by centrifugation and removal of the infranatant, whereafter an equal volume of 10% sucrose solution was added. The resulting dispersion was lyophilised and then redispersed in distilled water, yielding a milky white microbubble dispersion with a volume median diameter of 3.5 µm, measured using a Coulter Counter.

c) 2-Methylbutane Emulsion

Hydrogenated phosphatidylserine (100 mg) in purified water (20 ml) was heated to 80° C. for 5 minutes and the resulting dispersion was cooled to 0° C. overnight. 1 ml of the dispersion was transferred to a 2 ml vial, to which was added 200 µl of 2-methylbutane (b.p. 28° C.). The vial was then shaken for 45 seconds using a CapMix® to yield an emulsion of diffusible component which was stored at 0° C. when not in use. The volume median diameter of the emulsion droplets was 1.9 µm, measured using a Coulter Counter.

d) Perfluoropentane Emulsion

The procedure of Example 1(c) was repeated except that the 2-methylbutane was replaced by perfluoropentane (b.p. 29° C.). The thus-obtained emulsion of diffusible component was stored at 0° C. when not in use.

e) 2-Chloro-1,1,2-trifluoroethyl difluoromethyl ether Emulsion

The procedure of Example 1(c) was repeated except that the 2-methylbutane was replaced by 2-chloro-1,1,2-trifluoroethyl difluoromethyl ether (b.p. 55–57° C.). The thus-obtained emulsion of diffusible component was stored at 0° C. when not in use.

f) 2-Bromo-2-chloro-1,1,1-trifluoroethane Emulsion

The procedure of Example 1(c) was repeated except that the 2-methylbutane was replaced by 2-bromo-2-chloro-1,1,1-trifluoroethane (b.p. 49° C.). The thus-obtained emulsion of diffusible component was stored at 0° C. when not in use.

g) 1-Chloro-2,2,2-trifluoroethyl difluoromethyl ether Emulsion

The procedure of Example 1(c) was repeated except that the 2-methylbutane was replaced by 1-chloro-2,2,2-trifluoroethyl difluoromethyl ether (b.p. 49° C.). The thus-obtained emulsion of diffusible component was stored at 0° C. when not in use.

h) Dispersion of Gas-containing Polymer/Human Serum Albumin Particles

Human serum albumin-coated gas-containing particles of polymer made from ethylidene bis(16-hydroxyhexadecanoate) and adipoyl chloride, prepared according to Example 3(a) of WO-A-9607434, (100 mg) were crushed in a mortar and dispersed in 0.9% aqueous sodium chloride (10 ml) by shaking on a laboratory shaker for 24 hours.

i) Dispersion of Gas-containing Polymer/Gelatin Particles

Gelatin-coated gas-containing particles of polymer made from ethylidene bis(16-hydroxyhexadecanoate) and adipoyl chloride, prepared according to Example 3(e) of WO-A-9607434, (100 mg) were crushed in a mortar and dispersed in 0.9% aqueous sodium chloride (10 ml) by shaking on a laboratory shaker for 24 hours.

j) 2-Methylbutane Emulsion

The procedure of Example 1(c) was repeated except that the emulsion was diluted 10 times prior to use and was stored in an ice bath when not in use.

k) Perfluoropentane Emulsion

The procedure of Example 1(d) was repeated except that the emulsion was diluted 10 times prior to use and was stored in an ice bath when not in use.

l) Perfluoropentane Emulsion

Hydrogenated phosphatidylserine (100 mg) in purified water (20 ml) was heated to 80° C. for 5 minutes and the resulting dispersion was cooled to 0° C. overnight. 1 ml of the dispersion was transferred to a 2 ml vial, to which was added 100 µl of perfluoro-n-pentane (b.p. 29° C.). The vial was then shaken for 75 seconds using a CapMix® to yield an emulsion of diffusible component which was stored at 0° C. when not in use. The volume median diameter of the emulsion droplets was 2.9 µm, measured using a Coulter Counter.

m) Perfluorobutane Emulsion

The procedure of Example 1(l) was repeated except that the perfluoropentane was replaced by perfluorobutane (b.p. −2° C.). The thus-obtained emulsion of diffusible component was stored at 0° C. when not in use.

n) Perfluoropentane Emulsion Prepared by Sonication

Hydrogenated phosphatidylserine (500 mg) in purified water (100 ml) was heated to 80° C. for 5 minutes and the resulting dispersion was allowed to cool to room temperature overnight. 10 ml of the dispersion were transferred to a 30 ml vial, to which perfluoropentane (1 ml) was then added. Sonication of the resulting mixture for two minutes gave a dispersion of diffusible component wherein the drops had a mean diameter <1 µm.

o) Perfluoropentane Emulsion

The procedure of Example 1(l) was repeated except that the volume of perfluoropentane employed was reduced to 60 µl. The thus-obtained emulsion of diffusible component was stored at 0° C. when not in use.

p) Perfluoropentane Emulsion

The procedure of Example 1(l) was repeated except that the volume of perfluoropentane employed was reduced to 20 μl. The thus-obtained emulsion of diffusible component was stored at 0° C. when not in use.

q) Perfluoropentane:perfluoro-4-methylpent-2-ene (1:1) Emulsion

The procedure of Example 1(l) was repeated except that the perfluoropentane was replaced by a mixture of 50 μl of perfluoropentane (b.p. 29° C.) and 50 μl of perfluoro-4-methylpent-2-ene (b.p. 49° C.). The thus-obtained emulsion of diffusible components was stored at 0° C. when not in use. The volume median diameter of the emulsion droplets was 2.8 μm, measured using a Coulter Counter.

r) Perfluoropentane:1H,1H,2H-heptafluoropent-1-ene (1:1) Emulsion

The procedure of Example 1(l) was repeated except that the perfluoropentane was replaced by a mixture of 50 μl of perfluoropentane (b.p. 29° C.) and 50 μl of 1H,1H,2-H-heptafluoropent-1-ene (b.p. 30–31° C.). The thus-obtained emulsion of diffusible components was stored at 0° C. when not in use.

s) Perfluoropentane Emulsion Stabilised by distearoylphosphatidylcholine:distearoylphosphatidylserine (1:1)

The procedure of Example 1(l) was repeated except that the hydrogenated phosphatidylserine was replaced by a mixture of distearoylphosphatidylcholine (50 mg) and distearoylphosphatidylserine, sodium salt (50 mg). The thus-obtained emulsion of diffusible component was stored at 0° C. when not in use.

t) Perfluoropentane Emulsion Stabilised By distearoylphosphatidylcholine:distearoylphosphatidylserine (3:1)

The procedure of Example 1(l) was repeated except that the hydrogenated phosphatidylserine was replaced by a mixture of distearoylphosphatidylcholine (75 mg) and distearoylphosphatidylserine, sodium salt (25 mg). The thus-obtained emulsion of diffusible component was stored at 0° C. when not in use.

u) Perfluoropentane Emulsion Stabilised By distearoylphosphatidylcholine:distearoylphosphatidylglycerol (3:1)

The procedure of Example 1(l) was repeated except that the hydrogenated phosphatidylserine was replaced by a mixture of distearoylphosphatidylcholine (75 mg) and distearoylphosphatidylglycerol, sodium salt (25 mg). The thus-obtained emulsion of diffusible component was stored at 0° C. when not in use.

v) Perfluoropentane Emulsion Stabilised By Hydrogenated phosphatidylcholine:hydrogenated phosphatidylserine (11:1)

The procedure of Example 1(l) was repeated except that the hydrogenated phosphatidylserine was replaced by 100 mg of a mixture of hydrogenated phosphatidylcholine and hydrogenated phosphatidylserine (11:1). The thus-obtained emulsion of diffusible component was stored at 0° C. when not in use.

w) Perfluoro-4-methylpent-2-ene Emulsion Stabilised by distearoylphosphatidylcholine:distearoylphosphatidylserine (3:1)

The procedure of Example 1(l) was repeated except that the hydrogenated phosphatidylserine was replaced by a mixture of distearoylphosphatidylcholine (75 mg) and distearoylphosphatidylserine, sodium salt (25 mg) and the perfluoropentane was replaced by perfluoro-4-methylpent-2-ene. The thus-obtained emulsion of diffusible component was stored at 0° C. when not in use.

x) Perfluoropentane:perfluoro-4-methylpent-2-ene (1:1) Emulsion Stabilised by distearoylphosphatidylcholine:distearoylphosphatidylserine (3:1)

The procedure of Example 1(w) was repeated except that the perfluoro-4-methylpent-2-ene was replaced by a mixture of 50 μl of perfluoropentane and 50 μl of perfluoro-4-methylpent-2-ene. The thus-obtained emulsion of diffusible components was stored at 0° C. when not in use.

y) Perfluoropentane:perfluoro-4-methylpent-2-ene (1:1) Emulsion Stabilised by distearoylphosphatidylcholine:distearoylphosphatidylglycerol (3:1)

The procedure of Example 1(x) was repeated except that the distearoylphosphatidylserine, sodium salt was replaced by distearoylphosphatidylglycerol, sodium salt. The thus-obtained emulsion of diffusible components was stored at 0° C. when not in use.

z) Perfluorodecalin:perfluorobutane Emulsion

Hydrogenated phosphatidylserine (100 mg) in aqueous glycerol (5.11%)/propylene glycol (1.5%) (20 ml) was heated to 80° C. for 5 minutes and the resulting dispersion was cooled to 0° C. overnight. 1 ml of the dispersion was transferred to a 2 ml vial, to which was added 100 μl of perfluorodecalin (b.p. 141–143° C.) saturated with perfluorobutane (b.p. −2° C.). The vial was then shaken for 60 seconds using a CapMix® to yield an emulsion of diffusible component which was stored at 0° C. when not in use.

aa) Perfluorodecalin:perfluoropropane Emulsion

The procedure of Example 1(z) was repeated except that the perfluorodecalin saturated with perfluorobutane was replaced by perfluorodecalin saturated with perfluoropropane (b.p. −39° C.). The thus-obtained emulsion of diffusible component was stored at 0° C. when not in use.

ab) Perfluorodecalin:sulphur hexafluoride Emulsion

The procedure of Example 1(z) was repeated except that the perfluorodecalin saturated with perfluorobutane was replaced by perfluorodecalin saturated with sulphur hexafluoride (b.p. −64° C.). The thus-obtained emulsion of diffusible component was stored at 0° C. when not in use.

ac) Perfluoropentane Emulsion Stabilised with Fluorad FC-170C 1 ml of a dispersion of Fluorad FC-170C (200 mg) in purified water (20 ml) was transferred to a 2 ml vial, to which was added 100 μl of perfluoro-n-pentane. The vial was then shaken for 75 seconds using a CapMix® to yield an emulsion of diffusible component which was stored at 0° C. when not in use.

ad) Perfluoropentane Emulsion Stabilised with Pluronic F68:Fluorad FC-170C

100 μl of a 10% Pluronic F68 solution was added to 200 μl of 1% Fluorad FC170C and 700 μl purified water. The resulting mixture was transferred to a 2 ml vial, to which was added 100 μl of perfluoro-n-pentane. The vial was then shaken for 75 seconds using a CapMix® to yield an emulsion of diffusible component which was stored at 0° C. when not in use. A sample of this emulsion was transferred to a screw-topped plastic vial (2.8 ml) which was then sonicated in a water bath for 2 minutes (pulse sonication: 1 per second). The volume median diameter of the sonicated emulsion droplets was 0.99 μm, measured using a Coulter Counter.

ae) Perfluoropentane Emulsion Stabilised with Pluronic F68:Fluorad FC-170C and Prepared by Homogenisation 1 ml of a 10% Pluronic F68 solution was added to 2 ml of 1% Fluorad FC170C and 7 ml purified water, whereafter 1 ml of perfluoro-n-pentane was added to the resulting mixture. The thus-obtained dispersion was then homogenised by rotor/stator homogenisation for 2 minutes at 23000 rpm. The resulting emulsion was transferred to a screw-topped plastic vial (10 ml) and sonicated in a water bath for 2 minutes (pulse sonication: 1 per second).

af) Perfluoropentane Emulsion

Hydrogenated phosphatidylserine (250 mg) in purified water (100 ml) was heated to 80° C. for 5 minutes and the resulting dispersion was cooled to 0° C. overnight. 1 ml of the dispersion was transferred to a 2 ml vial, to which was added 100 μl of perfluoropentane. The vial was shaken for 75 seconds using a CapMix® to yield an emulsion of diffusible component which was stored at 0° C. when not in use.

ag) Dispersion of Lyophilised Perfluorobutane Gas Dispersion

A sample of the milky white dispersion from Example 1(a) was washed three times by centrifugation and removal of the infranatant, whereafter an equal volume of 10% sucrose solution was added. The resulting dispersion was lyophilised and then redispersed in distilled water, yielding a milky white microbubble dispersion with a volume mean diameter of 2.6 μm, measured using a Coulter Counter.

ah) Perfluoropropane Gas Dispersion

The procedure of Example 1(a) was repeated except that the perfluorobutane gas was replaced by perfluoropropane gas. The resulting milky white microbubble dispersion had a volume median diameter of 2.6 μm, measured using a Coulter Counter.

ai) Perfluoropentane Emulsion

Hydrogenated phosphatidylserine (100 mg) in purified water (100 ml) was heated to 80° C. for 5 minutes and the resulting dispersion was cooled to 0° C. overnight. 1 ml of the dispersion was transferred to a 2 ml vial, to which was added 100 μl of perfluoropentane. The vial was shaken for 75 seconds using a CapMix® to yield an emulsion of diffusible component which was stored at 0° C. when not in use.

aj) Perfluoropentane Emulsion Stabilised with Brij 58: Fluorad FC-170C Prepared by Shaking Brij 58 (400 mg) was added to a solution of 0.1% Fluorad FC-170C (10 ml) and stirred at room temperature for one hour. 1 ml of the resulting solution was transferred to a 2 ml vial, to which was added perfluoropentane (100 μl). The vial was then shaken for 75 seconds using a CapMix® to yield an emulsion of diffusible component which was stored at 0° C. when not in use.

ak) Perfluoropentane Emulsion Stabilised with Brij58: Fluorad FC-170C Prepared by Sonication Brij58 (400 mg) was added to a solution of 0.1% Fluorad FC-170C (10 ml) and stirred at room temperature for one hour. Perfluoropentane (1 ml) was then added and the resulting mixture was sonicated for 2 minutes to yield an emulsion of small drops of the diffusible component. This emulsion was stored at 0° C. when not in use.

al) Perfluoro-4-methylpent-2-ene Emulsion

The procedure of Example 1(l) was repeated except that the perfluoropentane was replaced by perfluoro-4-methylpent-2-ene (b.p. 49° C.). The thus-obtained emulsion of diffusible component was stored at 0° C. when not in use.

am) 1H,1H,2H-Heptafluoropent-1-ene Emulsion

The procedure of Example 1(l) was repeated except that the perfluoropentane was replaced by 1H,1H,2-H-heptafluoropent-1-ene (b.p. 30–31° C.). The thus-obtained emulsion of diffusible component was stored at 0° C. when not in use.

an) Perfluorocyclopentene Emulsion

The procedure of Example 1(l) was repeated except that the perfluoropentane was replaced by perfluorocyclopentene (b.p. 27° C.). The thus-obtained emulsion of diffusible component was stored at 0° C. when not in use.

ao) Perfluorodimethylcyclobutane Emulsion

The procedure of Example 1(l) was repeated except that the perfluoropentane was replaced by perfluorodimethylcyclobutane (mixture of 1,2- and 1,3-isomers, b.p. 45° C.). The thus-obtained emulsion of diffusible component was stored at 0° C. when not in use.

ap) Emulsion of an azeotropic perfluorohexane:n-pentane Mixture 4.71 g (0.014 mol) perfluoro-n-hexane (boiling point 59° C.)(Fluorochem Ltd.) and 0.89 g (0.012 mol) n-pentane (boiling point 36° C.) (Fluka AG) were mixed in a vial to give an azeotropic mixture shown to boil readily at 35° C. In another vial, hydrogenated phosphatidylserine (100 mg) in purified water (20 ml) was heated to 80° C. for 5 minutes and the resulting dispersion was cooled to room temperature. 1 ml of the phospholipid dispersion was transferred to a 2 ml vial to which was added 100 μl of the azeotropic mixture. The vial was then shaken for 45 seconds using a CapMix® to yield an emulsion of diffusible component which was stored at room temperature when not in use.

aq) Perfluorodimethylcyclobutane Emulsion

The procedure of Example 1(l) was repeated except that the perfluoropentane was replaced by perfluorodimethylcyclobutane (>97% 1,1-isomer, balance being 1,2- and 1,3-isomers). The thus-obtained emulsion of diffusible component was stored at 0° C. when not in use.

ar) Perfluorohexane Emulsion

The procedure of Example 1(l) was repeated except that the perfluoropentane was replaced by perfluorohexane (b.p. 57° C.). The thus-obtained emulsion of diffusible component was stored at 0° C. when not in use.

as) Perfluorodimethylcyclobutane Emulsion Stabilised with Fluorinated Surfactant The procedure of Example 1(aq) is repeated except that the hydrogenated phosphatidylserine is, replaced by either perfluorinated distearoylphosphatidylcholine (5 mg/ml) or a mixture of perfluorinated distearoylphosphatidylcholine and hydrogenated phosphatidylserine (3:1, total lipid concentration 5 mg/ml). The thus-obtained emulsions of diffusible component was stored at 0° C. when not in use.

at) 2,2,3,3,3-Pentafluoropropyl methyl ether Emulsion

The procedure of Example 1(l) was repeated except that the perfluoropentane was replaced by 2,2,3,3,3-pentafluoropropyl methyl ether (b.p. 46° C.). The thus-obtained emulsion of diffusible component was stored at 0° C. when not in use.

au) 2H,3H-Decafluoropentane Emulsion

The procedure of Example 1(l) was repeated except that the perfluoropentane was replaced by 2H,3-H-decafluoropentane (b.p. 54° C.). The thus-obtained emulsion of diffusible component was stored at 0° C. when not in use.

av) Perfluorodimethylcyclobutane Emulsion Stabilised by Lysophosphatidylcholine

The procedure of Example 1(aq) was repeated except that the hydrogenated phosphatidylserine was replaced by lysophosphatidylcholine. The thus-obtained emulsion of diffusible component was stored at 0° C. when not in use.

aw) Perfluorodimethylcyclobutane Emulsion Stabilised by Hydrogenated phosphatidylserine:lysophosphatidylcholine (1:1)

The procedure of Example 1(aq) was repeated except that the hydrogenated phosphatidylserine was replaced by a mixture of hydrogenated phosphatidylserine and lysophosphatidylcholine (1:1). The thus-obtained emulsion of diffusible component was stored at 0° C. when not in use.

ax) Perfluorodimethylcyclobutane Emulsion Stabilised by a polyethylene glycol 10,000-based Surfactant The procedure of Example 1(aq) was repeated except that the hydrogenated phosphatidylserine dispersion was replaced by a solution of α-(16-hexadecanoyloxy-hexadecanoyl)-ω-methoxypolyethylene glycol 10,000 in water (10 mg/ml). The thus-obtained emulsion of diffusible component was stored at 0° C. when not in use.

ay) Perfluorodimethylcyclobutane Emulsion Stabilised by a polyethylene glycol 10,000-based Surfactant The procedure of Example 1(aq) was repeated except that the hydrogenated phosphatidylserine dispersion was replaced by a solution of α-(16-hexadecanoyloxy-hexadecanoyl)-ω-methoxypolyethylene glycol 10,000 in water (20 mg/ml). The thus-obtained emulsion of diffusible component was stored at 0° C. when not in use.

az) Perfluorobutane-filled Microbubbles Encapsulated by phosphatidylserine and RGDC-Mal-polyethylene glycol 2000-distearoylphosphatidylethanolamine To a mixture of phosphatidylserine (4.5 mg) and Mal-polyethylene glycol 2000-distearoylphosphatidylethanolamine (0.5 mg) in a vial was added a solution of 1.4% propylene glycol/2.4% glycerol in water (1 ml). The dispersion was heated to 80° C. for 5 minutes, cooled to room temperature and then flushed with perfluorobutane gas. The vial was shaken for 45 seconds using a CapMix® and then placed on a roller table. After centrifugation the infranatant was exchanged with a solution of RGDC in sodium phosphate buffer having a pH of 7.5, after which the vial was placed on the roller table for several hours.

ba) Perfluorobutane-filled Microbubbles Encapsulated by phosphatidylserine and dipalmitoylphosphatidylethanolamine-polyethylene glycol 2000

To a vial containing phosphatidylserine and dipalmitoylphosphatidylethanolamine-polyethylene glycol 2000 (ratio 10:1) is added a solution of 2% propylene glycol in water to give a lipid concentration of 5 mg/ml. The dispersion is heated to 80° C. for 5 minutes and then cooled to room temperature, whereafter the headspace is flushed with perfluorobutane gas. The vial is shaken for 45 seconds using a CapMix® and is then placed on a roller table. After washing by centrifugation and removal of infranatant, an equal volume of water containing 10% sucrose is added. The resulting dispersion is lyophilised and then redispersed by adding water, yielding a milky white microbubble dispersion.

bb) Perfluorobutane-filled Microbubbles Encapsulated by phosphatidylserine and distearoylphosphatidylethanolamine-polyethylene glycol 5000

To a vial containing phosphatidylserine and distearoylphosphatidylethanolamine-polyethylene glycol 5000 (ratio 10:1) is added a solution of 2% propylene glycol in water to give a lipid concentration of 5 mg/ml. The dispersion is heated to 80° C. for 5 minutes and then cooled to room temperature, whereafter the headspace is flushed with perfluorobutane gas. The vial is shaken for 45 seconds using a CapMix® and is then placed on a roller table. After washing by centrifugation and removal of infranatant, an equal volume of water containing 10% polyethylene glycol is added. The resulting dispersion is lyophilised and then redispersed, yielding a milky white microbubble dispersion.

bc) Perfluorobutane-filled Microbubbles Encapsulated by phosphatidylserine and dipalmitoylphosphatidylethanolamine-polyethylene glycol 2000

To a vial containing phosphatidylserine and dipalmitoylphosphatidylethanolamine-polyethylene glycol 2000 (ratio 10:1) is added a solution of 2% propylene glycol in water to give a lipid concentration of 5 mg/ml. The dispersion is heated to 80° C. for 5 minutes and then cooled to room temperature, whereafter the headspace is flushed with perfluorobutane gas. The vial is shaken for 45 seconds using a CapMix® and is then placed on a roller table. After washing by centrifugation and removal of infranatant, an equal volume of water is added, yielding a milky white microbubble dispersion.

bd) Perfluorobutane-filled Microbubbles Encapsulated by phosphatidylserine and distearoylphosphatidylethanolamine-polyethylene glycol 5000

To a vial containing phosphatidylserine and distearoylphosphatidylethanolamine-polyethylene glycol 5000 (ratio 10:1) is added a solution of 2% propylene glycol in water to give a lipid concentration of 5 mg/ml. The dispersion is heated to 80° C. for 5 minutes and then cooled to room temperature, whereafter the headspace is flushed with perfluorobutane gas. The vial is shaken for 45 seconds using a CapMix® and is then is placed on a roller table. After washing by centrifugation and removal of infranatant, an equal volume of water is added, yielding a milky white microbubble dispersion.

be) Perfluorodimethylcyclobutane Emulsion Stabilised by phosphatidylserine and dipalmitoylphosphatidylethanolamine-polyethylene glycol 2000

The procedure of Example 1(aq) is repeated except that the hydrogenated phosphatidylserine is replaced by a mixture of hydrogenated phosphatidylserine and dipalmitoylphosphatidylethanolamine-polyethylene glycol 2000 (ratio 10:1). The thus-obtained emulsion of diffusible component is stored at 0° C. when not in use.

bf) Perfluorodimethylcyclobutane Emulsion Stabilised by phosphatidylserine and distearoylphosphatidylethanolamine-polyethylene glycol 5000

The procedure of Example 1(aq) is repeated except that the hydrogenated phosphatidylserine is replaced by a mixture of hydrogenated phosphatidylserine and distearoylphosphatidylethanolamine-polyethylene glycol 5000 (ratio 10:1). The thus-obtained emulsion of diffusible component is stored at 0° C. when not in use.

bg) Lyophilised perfluorobutane-filled Microbubbles Redispersed in an Emulsion

A sample of the milky white dispersion prepared as described in Example 1(bp) was washed three times by centrifugation and removal of the infranatant, whereafter an equal volume of 10% sucrose solution was added. The resulting dispersion was lyophilised and then redispersed in an emulsion prepared as described in Example 1(aq) just prior to use.

bh) Avidinylated perfluorodimethylcyclobutane Emulsion Droplets

Distearoylphosphatidylserine (4.5 mg) and biotin-dipalmitoylphosphatidylethanolamine (0.5 mg) were weighed into a clean vial and 1.0 ml of a solution of 2% propylene glycol was added. Following heating to 80° C. the mixture was cooled to room temperature. 100 μl of perfluorodimethylcyclobutane were added and the vial was shaken for 75 seconds using a CapMix® to yield an emulsion of diffusible component. A diluted sample of the emulsion (100 μl emulsion in 1 ml water) was incubated with excess avidin and placed on a roller table. The diluted emulsion was then washed extensively with water and concentrated by centrifuging.

bi) 1H-Tridecafluorohexane Emulsion

The procedure of Example 1(l) was repeated except that the perfluoropentane was replaced by 1H-tridecafluorohexane (b.p. 71° C.). The thus-obtained emulsion of diffusible component was stored at 0° C. when not in use.

bj) Perfluoroheptane Emulsion

The procedure of Example 1(l) was repeated except that the perfluoropentane was replaced by perfluoroheptane (b.p. 80–85° C.). The thus-obtained emulsion of diffusible component was stored at 0° C. when not in use.

bk) Perfluorodimethylcyclobutane Emulsion with phosphatidylserine and fluorescent streptavidin Distearoylphosphatidylserine (4.5 mg) and biotin-dipalmitoylphosphatidylethanolamine (0.5 mg) are weighed into a clean vial and 1.0 ml of a solution of 2% propylene glycol is added. Following heating to 80° C. the mixture is cooled to room temperature. 100 μl of perfluorodimethylcyclobutane are added and the vial is shaken for 75 seconds using a CapMix® mixer to yield an emulsion of diffusible component. A diluted sample of the emulsion (100 μl emulsion in 1 ml water) is incubated with excess fluorescent streptavidin in phosphate buffer and placed on a roller table. The diluted emulsion is then washed extensively with water and concentrated by centrifuging.

bl) Dispersion of Lyophilised perfluorobutane Gas Dispersion

A sample of the milky white dispersion prepared as described in Example 1(a) was washed three times by centrifugation and removal of the infranatant, whereafter an equal volume of 10% sucrose solution was added. The resulting dispersion was lyophilised and then redispersed in distilled water just prior to use.

bm) Perfluorodimethylcyclobutane Emulsion Stabilised by Sterilised phosphatidylserine The procedure of Example 1(aq) was repeated except that the hydrogenated phosphatidylserine was replaced by a sterilised solution of hydrogenated phosphatidylserine. The thus-obtained emulsion of diffusible component was stored at 0° C. when not in use.

bn) Perfluoropropane Gas Dispersion

The procedure of Example 1(a) was repeated except that the perfluorobutane gas was replaced by perfluoropropane gas.

bo) Dispersed Echovist

Echovist granulate (Schering AG) (0.25 g) was dispersed in an emulsion (1.15 ml) prepared as described in Example 1(aq).

bp) Perfluorobutane Gas Dispersion

Hydrogenated phosphatidylserine (500 mg) was added to a solution of 1.5% propylene glycol/5.11% glycerol in water (100 ml) and heated to 80° C. for 5 minutes, whereafter the resulting dispersion was allowed to cool to ambient temperature. 1 ml portions were transferred to 2 ml vials, the headspace above each portion was flushed with perfluorobutane gas, and the vials were shaken for 45 seconds using a CapMix®, whereafter the vials were placed on a roller table.

bq) Preparation of Biotinylated Perfluorobutane Microbubbles

Distearoylphosphatidylserine (4.5 mg) and biotin-dipalmitoylphosphatidylethanolamine (0.5 mg) were weighed into a clean vial and 1.0 ml of a solution of 1.4% propylene glycol/2.4% glycerol was added. Following heating to 78° C. the mixture was cooled to room temperature and the head space was flushed with perfluorobutane gas. The vial was shaken for 45 seconds using a CapMix® mixer and was then placed on a roller table for 16 hours. The resulting microbubbles were washed extensively with deionised water.

br) Aerogels

To "spatula edge," pyrolysed resorcinol-formaldehyde aerogel particles (provided by Dr. Pekala, Lawrence Livermore National Laboratory) were added 300 μl water, a droplet of pH9 buffer and 5–10 droplets of 1% Pluronic F68. The aerogel particles sedimented quickly, but did not aggregate.

bs) Small Bubbles

A rubber tube, 8 mm inner diameter and approximately 20 cm long, was placed vertically in a stand, capped at the bottom end and filled with a microbubble dispersion made according to Example 1(a) (except that an Ystral® rotor stator homogeniser was used to make the microbubble dispersion). After two hours, a syringe connected to a canula was inserted into the rubber tube close to the bottom, and a 1 ml fraction of the size-fractionated microbubble dispersion was collected. Coulter counter analysis revealed the thus-obtained microbubble dispersion to have a median diameter of 1.2 μm.

bt) Perfluorobutane Gas Dispersion Stabilised by 5% Albumin:5% Dextrose (1:3)

20% human serum was diluted to 5% with purified water. A 5 ml sample of the diluted albumin was further diluted with 5% glucose (15 ml) and the resulting mixture was transferred to a vial. The head space was flushed with perfluorobutane gas and the vial was sonicated for 80 seconds, giving a milky white microbubble dispersion.

bu) Dispersion of Buckminsterfullerene $C_{60}$

Buckminsterfullerene $C_{60}$ was added to 2.5% human serum albumin (1 ml) in a 2 ml vial which was shaken for 75 seconds using a CapMix®.

bv) Sulphur Hexafluoride Gas Dispersion

Distearoylphosphatidylcholine:dipalmitoylphosphatidylglycerol (10:1) stabilised microbubbles were made as described in Example 5 of WO-A-9409829. Thus 50 mg distearoylphosphatidylcholine, 5 mg dipalmitoylphosphatidylglycerol and 2.2 g polyethylene glycol 4000 were dissolved in 22 ml t-butanol at 60° C., and the solution was rapidly cooled to −77° C. and lyophilised overnight. 100 mg of the resulting powder were placed in a vial, and the head space was evacuated and then filled with sulphur hexafluoride. 1 ml purified water was added just before use, giving a microbubble dispersion.

bw) 2-Methylbutane Emulsion

Hydrogenated phosphatidylserine (100 mg) in purified water (20 ml) was heated to 80° C. for 5 minutes and the resulting dispersion was cooled in refrigerator overnight. 1 ml of the dispersion was transferred to a 2 ml vial, to which was added 100 μl of 2-methylbutane. The vial was shaken for 75 seconds using a CapMix® to yield an emulsion of diffusible component which was stored at 0° C. when not in use.

bx) Lyophilised Perfluorobutane Gas Dispersion in Aqueous Sodium Bicarbonate

A sample of the milky white dispersion from Example 1(a) was washed three times by centrifugation and removal of the infranatant, whereafter an equal volume of 10% sucrose solution was added. The resulting dispersion was lyophilised and then redispersed in 0.1M sodium bicarbonate solution.

by) Perfluorobutane Gas Dispersion

A perfluorobutane gas dispersion was prepared as Example 1(a). The dispersion was washed three times with purified water by centrifugation and removal of the infranant, yielding a milky white microbubble dispersion.

bz) Perfluorobutane Gas Dispersion with Iron Oxide Particles

To 1 ml of a perfluorobutane gas dispersion prepared as in Example 1(by) was added 1 ml purified water. The pH was raised to 11.2 with ammonium hydroxide and the dispersion was heated for 5 minutes at 60° C. Uncoated iron oxide particles (0.3 ml, 4.8 mg Fe/ml) were added and the dispersion was allowed to stand for 5 minutes. The pH was lowered to 5.9 with hydrochloric acid, yielding a brown dispersion which after a while gave a top layer with brown particles, a clear non-coloured infranant and no precipitate.

ca) Perfluorobutane Gas Dispersion with Iron Oxide Particles

To 1 ml of a perfluorobutane gas dispersion prepared as in Example 1(by) was added 0.3 ml uncoated iron oxide particles (4.8 mg Fe/ml) at pH 7, yielding a brown dispersion which on standing gave a top layer with brown microbubbles, a clear infranant and no precipitate.

cb) Comparatives

To 1 ml of a solution of hydrogenated phosphatidylserine in purified water (5 mg/ml) was added 0.3 ml uncoated iron oxide particles (4.8 mg Fe/ml) yielding a brown dispersion which after standing gave a brown precipitate.

cc) Perfluorobutane Gas Dispersion with Iron Oxide Particles Coated with Oleic Acid 1.3 mmol $FeCl_2 \cdot 4H_2O$ (0.259 g) and 2.6 mmol $FeCl_3 \cdot 6H_2O$ (0.703 g) were dissolved in 10 ml purified water and 1.5 ml ammonium hydroxide were added. The resulting iron oxide particles were washed five times with purified water (25 ml). Diluted ammonium hydroxide was added to the particles and the suspension was heated to 80° C. Oleic acid (0.15 g) was added, and the dispersion was allowed to stand for 5 minutes at ambient temperature. Purified water (10 ml) was added and the pH was lowered to 5.4 with hydrochloric acid. The dispersion was sonicated for 15 minutes, whereafter the infranant was removed and the particles were suspended in 2-methylbutane (5 ml), yielding a fine black dispersion.

25 mg distearoylphosphatidylcholine and 2.5 mg dimyristoylphosphatidylglycerol were dissolved in 11 ml t-butanol at 60° C. and 0.1 ml iron oxide particles from above was added, together with 1.1 g polyethylene glycol 4000. The dispersion was heated for 10 minutes at 60° C., rapidly cooled to −77° C. and lyophilised. 100 mg of the lyophilisate were introduced into a 2 ml vial, which was then evacuated and flushed twice with perfluorobutane gas. The lyophilisate was then dispersed in 1 ml purified water and washed twice with purified water by centrifugation with removal of the infranant and the precipitate. After standing the resulting dispersion had a light grey and floating top layer.

EXAMPLE 2

In vitro Characterisation of Microbubble Growth by Microscopy/Visual Observation a) One drop of the perfluorobutane gas dispersion from Example 1(a) at ca. 4° C. was diluted with one drop of air-supersaturated purified water at ca. 4° C. on a microscope object glass cooled to ca. 4° C. and investigated at 400× magnification. The microbubbles were observed to vary in size from 2 to 5 $\mu$m. The temperature was then raised to ca. 40° C., whereupon a significant increase in the size of the microbubbles was observed, the larger microbubbles growing most in size. The number of microbubbles was significantly reduced after about 5 minutes.

b) [Comparative] One drop of the 2-methylbutane emulsion from Example 1(c), cooled in an ice bath to ca. 0° C., was placed on a microscope object glass cooled to ca. 0° C. and investigated at 400×magnification. The oil phase droplets of the emulsion were observed to vary in size from 2 to 6 $\mu$m. The temperature was then raised to ca. 40° C. No microbubble formation was observed.

c) A sample of the perfluorobutane gas dispersion from Example 1(a) (0.5 ml) was diluted with purified water (50 ml) and cooled to 0° C. A portion of this diluted disperion (1 ml) was mixed with a portion of the 2-methylbutane emulsion from Example 1(c) (100 $\mu$l). One drop of the resulting mixture was placed on a microscope object glass maintained at 0° C. by means of a heating/cooling stage and covered with a cover glass, also at 0° C. The temperature of the object glass was gradually increased to 40° C. using the heating/cooling stage. Rapid and substantial microbubble growth was observed by microscopy and was confirmed by size and distribution measurements made using a Malvern Mastersizer.

d) [Comparative] A sample of the perfluorobutane gas dispersion from Example 1(a) (0.5 ml) was diluted with purified water (50 ml) and cooled in an ice bath to 0° C. A portion of this diluted disperion (1 ml) was mixed with 100 $\mu$l of a 5 mg/ml dispersion of hydrogenated phosphatidylserine in purified water, also at 0° C. One drop of the resulting mixture was placed on a microscope object glass cooled to 0° C. and investigated at 400×magnification. The microbubbles were observed to vary in size from 2 to 5 $\mu$m. The temperature was then raised to ca. 40° C., whereupon a significant increase in the size of the microbubbles was observed, although the increase was less heavy and less rapid then that observed in Example 2(c).

e) A sample of the perfluorobutane gas dispersion from Example 1(a) was diluted with purified water (1:1) and cooled to 0° C. A drop of the 2-chloro-1,1,2-trifluoroethyl difluoromethyl ether emulsion from Example 1(e) was added to the diluted microbubble dispersion on a microscope object glass maintained at 0° C. by means of a heating/cooling stage and covered with a cover glass, also at 0° C. The temperature of the object glass was gradually increased to 40° C. using the heating/cooling stage. Rapid and substantial microbubble growth was observed by microscopy.

f) A sample of the perfluorobutane gas dispersion from Example 1(a) was diluted with purified water (1:1) and cooled to 0° C. A drop of the 2-bromo-2-chloro-1,1,1-trifluoroethane emulsion from Example 1(f) was added to the diluted microbubble dispersion on a microscope object glass maintained at 0° C. by means of a heating/cooling stage and covered with a cover glass, also at 0° C. The temperature of the object glass was gradually increased to 40° C. using the heating/cooling stage.

Rapid and substantial microbubble growth was observed by microscopy.

g) A sample of the perfluorobutane gas dispersion from Example 1(a) was diluted with purified water (1:1) and cooled to 0° C. A drop of the 1-chloro-2,2,2-trifluoroethyl difluoromethyl ether emulsion from Example 1(g) was added to the diluted microbubble dispersion on a microscope object glass maintained at 0° C. by means of a heating/cooling stage and covered with a cover glass, also at 0° C. The temperature of the object glass was gradually increased to 40° C. using the heating/cooling stage. Rapid and substantial microbubble growth was observed by microscopy.

h) One drop of the dispersion of polymer/human serum albumin microparticles from Example 1(h) and one drop of the perfluoropentane emulsion from Example 1(k) were placed on a microscope object glass warmed to 50° C. and investigated at 400×magnification. Significant growth of microbubbles was observed as the drops mixed.

i) One drop of the dispersion of polymer/human serum albumin microparticles from Example 1(h) and one drop of the 2-methylbutane emulsion from Example 1(j) were placed on a microscope object glass warmed to 40° C. and investigated at 400×magnification. Significant, rapid and heavy growth of microbubbles was observed as the drops mixed.

j) One drop of the dispersion of polymer/gelatin microparticles from Example 1(i) and one drop of the perfluoropentane emulsion from Example 1(k) were placed on a microscope object glass warmed to 50° C. and investigated at 400×magnification. Significant growth of microbubbles was observed as the drops mixed.

k) One drop of the dispersion of polymer/gelatin microparticles from Example 1(i) and one drop of the 2-methylbutane emulsion from Example 1(j) were placed on a microscope object glass warmed to 40° C. and investigated at 400×magnification. Significant, rapid and heavy growth of microbubbles was observed as the drops mixed.

l) [Comparative] One drop of the perfluoropentane emulsion from Example 1(k) was placed on a microscope object glass warmed to 50° C. and investigated at 400× magnification. No microbubble formation was observed.

m) [Comparative] One drop of the 2-methylbutane emulsion from Example 1(j) was placed on a microscope object glass warmed to 40° C. and investigated at 400× magnification. No microbubble formation was observed.

n) [Comparative] One drop of the dispersion of polymer/ human serum albumin microparticles from Example 1(h) is placed on a microscope object glass warmed to 40° C. and investigated at 400×magnification. No significant change is seen.

o) [Comparative] One drop of the dispersion of polymer/ gelatin microparticles from Example 1(i) is placed on a microscope object glass warmed to 50° C. and investigated at 400×magnification. No significant change is seen.

p) One drop of a dispersion of human serum albumin-stabilised air microbubbles prepared as described in U.S. Pat. No. 4,718,433 and one drop of the 2-methylbutane emulsion from Example 1(j) were placed on a microscope object glass at 20° C. and investigated at 400×magnification. Significant growth of microbubbles was observed as the drops mixed.

q) A sample of the perfluorobutane gas dispersion from Example 1(a) was diluted with purified water (1:1) and cooled to 0° C. A drop of the perfluorodecalin/ perfluorobutane emulsion from Example 1(z) was added to the diluted microbubble dispersion on a microscope object glass maintained at 0° C. by means of a heating/cooling stage and covered with a cover glass, also at 0° C. The temperature of the object glass was gradually increased to 40° C. using the heating/cooling stage. Rapid and substantial microbubble growth was observed by microscopy.

r) A sample of the perfluorobutane gas dispersion from Example 1(a) was diluted with purified water (1:1) and cooled to 0° C. A drop of the perfluorodecalin/ perfluoropropane emulsion from Example 1(aa) was added to the diluted microbubble dispersion on a microscope object glass maintained at 0° C. by means of a heating/ cooling stage and covered with a cover glass, also at 0° C. The temperature of the object glass was gradually increased to 40° C. using the heating/cooling stage. Rapid and substantial microbubble growth was observed by microscopy.

s) A sample of the perfluorobutane gas dispersion from Example 1(a) was diluted with purified water (1:1) and cooled to 0° C. A drop of the perfluorodecalin/sulphur hexafluoride emulsion from Example 1(ab) was added to the diluted microbubble dispersion on a microscope object glass maintained at 0° C. by means of a heating/cooling stage and covered with a cover glass, also at 0° C. The temperature of the object glass was is gradually increased to 40° C. using the heating/cooling stage, whereupon an increase in the size of the microbubbles was observed after 4–5 minutes, although the increase was less heavy and less rapid then that observed in Examples 2(q) and 2(r).

t) A sample of the perfluorobutane gas dispersion from Example 1(a) was diluted with purified water (1:1) and cooled to 0° C. A drop of the Pluronic F68-stabilised perfluoropentane emulsion from Example 1(ad) was added to the diluted microbubble dispersion on a microscope object glass maintained at 0° C. by means of a heating/ cooling stage and covered with a cover glass, also at 0° C. The temperature of the object glass was gradually increased to 40° C. using the heating/cooling stage. Rapid and substantial microbubble growth was observed by microscopy.

u) One drop of the perfluorobutane gas dispersion from Example 1(a) and one drop of the Brij58:Fluorad FC-170C-stabilised perfluoropentane emulsion from Example 1(aj) were placed on a microscope object glass warmed to 40° C. and investigated at 400×magnification. After a while slow microbubble growth was observed.

v) One drop of the perfluorobutane gas dispersion from Example 1(a) and one drop of the Brij58:Fluorad FC-170C-stabilised perfluoropentane emulsion from Example 1(ak) were placed on a microscope object glass warmed to 40° C. and investigated at 400×magnification. After a while microbubble growth was observed.

w) One drop of the perfluorobutane a gas dispersion from Example 1(a) and one drop of the perfluoro-4-methylpent-2-ene emulsion from Example 1(al) were placed on a microscope object glass warmed to 40° C. and investigated at 400×magnification. After a while slow microbubble growth was observed.

x) One drop of the perfluorobutanes gas dispersion from Example 1(a) and one drop of the 1H,1H,2-H-heptafluoropent-1-ene emulsion from Example 1(am) were placed on a microscope object glass warmed to 40° C. and investigated at 400×magnification. Significant and rapid microbubble growth was observed as the drops mixed.

y) One drop of the perfluorobutane gas dispersion from Example 1(a) and one drop of the perfluorocyclopentene emulsion from Example 1(an) were placed on a microscope object glass warmed to 40° C. and investigated at 400× magnification. Significant, rapid and heavy microbubble growth was observed as the drops mixed.

z) 400 µl of a perfluorobutane gas dispersion prepared as in Example 1(b) was transferred to a 2 ml vial at room temperature, and 100 µl of the azeotropic emulsion of Example 1(ap) was added. One droplet of the microbubble/ emulsion mixture was placed on a microscope object glass maintained at 20° C. by means of a heating/cooling stage. The temperature of the object glass was rapidly raised to 37° C. using the heating/cooling stage. A substantial, spontaneous and rapid microbubble growth was observed.

aa) One drop of biotinylated microbubbles prepared as described in Example 1(bq) was added to one drop of emulsion prepared as described in Example 1(bh) on a microscope object glass warmed up to 60° C. and investigated at 400×magnification. Significant growth of microbubbles and accumulation of microbubbles at the aggregated emulsion droplets was seen.

ab) Microbubbles prepared as described in Example 1(bq) may be analysed by flow cytometry, e.g. by employing a fluorescent streptavidin emulsion prepared as described in Example 1(bk) to detect attachment of streptavidin to the biotinylated microbubbles.

ac) One drop of the Echovist dispersion prepared as described in Example 1(bo) was placed on an object glass for microscopy investigation and kept at 37° C. using a heating/cooling stage. The sample was covered with a cover glass and placed under a microscope. Significant bubble growth was observed.

ad) One drop of the aerogel dispersion from Example 1(br) was placed on an object glass for microscopy investigation and kept at 37° C. using a heating/cooling stage. The sample was covered with a cover glass and placed under a microscope. A droplet of 2-methylbutane emulsion (from Example 1(c) above, except that 100 µl 2-methylbutane was used instead of 200 µl) was added to the edge of the cover glass so that the emulsion penetrated into the aerogel dispersion. On increasing the temperature to approximately 60° C., microbubbles occurred from the aerogel particles.

ae) [Comparative] One drop of the aerogel dispersion from Example 1(br) was placed on an object glass for microscopy investigation and kept at 20° C. using a heating/cooling stage. The sample was covered with a cover glass and placed under a microscope and the temperature was raised to 60° C. No microbubble growth was observed.

af) One drop of the microbubble dispersion from Example 1(bs) was placed on an object glass for microscopy investigation. The sample was covered with a cover glass and placed under a microscope fitted with a heating/cooling stage keeping the sample temperature at 20° C. One droplet of 2-methylbutane emulsion from Example 1(c) above was added to the edge of the cover glass so that the emulsion penetrated the microbubble dispersion. No microbubble growth was observed during the mixing stage. The temperature was then raised to 40° C., whereupon substantial microbubble growth was observed.

ag) [Comparative] One drop of the microbubble dispersion from Example 1(bs) was placed on an object glass for microscopy investigation. The sample was covered with a cover glass and placed under a microscope fitted with a heating/cooling stage keeping the sample temperature at 20° C. When the temperature was raised to 40° C., no microbubble growth was observed.

ah) To Echovist granulate (Schering AG) on a microscope object glass was added one drop of solvent for Echovist granulate at ambient temperature. One drop of 2-methylbutane emulsion prepared as Example 1(bw) was added and investigated at 100×magnification. Significant growth of microbubbles was observed as the drops mixed.

ai) One drop of Levovist® prepared for injection and one drop of 2-methylbutane emulsion prepared as in Example 1(bw) were placed on a microscope object glass at ambient temperature and investigated at 400×magnification. Significant, rapid and heavy growth of microbubbles was observed as the drops mixed.

aj) One drop of perfluorobutane gas dispersion from Example 1(br) and one drop of 2-methylbutane emulsion prepared as Example 1(bw) were placed on a microscope object glass at ambient temperature and investigated at 400×magnification. Significant, rapid and heavy microbubble growth was observed as the drops mixed.

ak) One drop of 2-methylbutane emulsion prepared as Example 1(by) was added to one drop of Buckminsterfullerene $C_{60}$ dispersion from Example 1(bu) on a microscope object glass at 40° C. Significant, heavy and rapid growth of microbubbles was observed as the drops mixed.

al) One drop of 2-methylbutane emulsion prepared as Example 1(bw) was added to one drop of sulphur hexafluoride gas dispersion from Example 1(bv) on a microscope object glass at 40° C. Significant, rapid and heavy microbubble growth was observed as the drops mixed.

am) One drop of 0.5M hydrochloric acid was added to one drop of perfluorobutane gas dispersion in aqueous sodium bicarbonate from Example 1(bx) on a microscope object glass at ambient temperature. Rapid, heavy and short lived microbubble growth was observed as the drops mixed.

an) One drop of 2-methylbutane emulsion prepared as in Example 1(bw) was added to one drop of the perfluorobutane gas dispersion with iron oxide particles from Example 1(bz) on a microscope object glass at ambient temperature. Significant, heavy and rapid microbubble growth was observed as the drops mixed.

ao) One drop of 2-methylbutane emulsion prepared as in Example 1(bw) was added to one drop of the perfluorobutane gas dispersion with iron oxide particles from Example 1(ca) on a microscope object glass at ambient temperature. Significant, heavy and rapid microbubble growth was observed as the drops mixed.

ap) [Comparative] One drop of 2-methylbutane emulsion prepared as Example 1(bw) was added to one drop of the iron oxide particle dispersion from Example 1(cb) on a microscope object glass at ambient temperature. No microbubble formation was observed.

aq) One drop of 2-methylbutane emulsion prepared as in Example 1(bw) was added to one drop of the perfluorobutane gas dispersion with oleic acid-coated iron oxide particles from Example 1(cc) on a microscope object glass at ambient temperature. Significant, heavy and rapid microbubble growth was observed as the drops mixed.

ar) 1 ml of the microbubble dispersion prepared as described in Example 1(bp) was diluted with 50 ml water. One drop of the diluted dispersion was added to one drop of soda water on a microscope object glass at ambient temperature. Spontaneous microbubble growth was observed as the drops mixed.

as) 0.4 µl of a biotinylated microbubble dispersion prepared according to Example 1(bq) and 0.02 ml of perfluorodimethylcyclobutane emulsion prepared as described in Example 1(bh) are added sequentially to a beaker containing 200 ml of Isoton at 37° C. with continuous stirring. The mixture is incubated for 20 seconds. A beam of pulsed ultrasound (10 kHz repetition frequency, 100 µJ in each pulse) at 2.5 MHz is aimed through the solution, which is observed in sharp side light against a black background. A bright streak of larger bubbles is immediately observed in the beam path.

at) One drop of the microbubble dispersion prepared as in Example 1(bl) is placed on an object glass for microscopy examination. The sample is covered with a cover glass and placed under a microscope fitted with a heating/cooling stage, keeping the temperature at 20° C. One droplet of a perfluorodimethylcyclobutane emulsion prepared as in Example 1(as) is added to the edge of the cover glass so that the emulsion can penetrate the microbubble dispersion. On increasing the temperature to approximately 60° C., substantial microbubble growth is observed.

EXAMPLE 3

In vitro Microbubble Size and Distribution Characterization a) Measurements Using Malvern Mastersizer Microbubble growth and the change in size distribution following mixture with diffusible component were analysed using a Malvern Mastersizer 1002 fitted with a 45 mm lens and having a measuring range of 0.1–80 µm. The sample cell contained Isoton II (150 ml) and was connected to a thermostatted bath operable over the temperature range 9–37° C. A sample of the perfluorobutane gas dispersion from Example 1(a) (110 μl) was added to the sample cell and after equilibration a portion of the 2-methylbutane emulsion from Example 1(c) (500 μl) was added. The Isoton II solution was pumped through the Mastersizer and the thermostatted bath so as to pass the measuring cell every 30 seconds. Repeated measurements were carried cut every 30 seconds for 3 minutes. The temperature of the Isoton II solution was gradually increased an& further measurements were made. The perfluorobutane gas dispersion and the 2-methylbutane emulsion were also analysed separately using similar conditions.

Analysis of the perfluorobutane gas dispersion alone showed that at 9° C. 82% of the microbubbles were of size below 9.9 μm; this proportion was reduced to 31% when the temperature had increased to 37° C. This temperature change was accompanied by a corresponding increase in the proportion of microbubbles in the size range 15–80 μm, from 8% to 42%.

Following mixing of the perfluorobutane gas dispersion and 2-methylbutane emulsion at 9° C. a slight increase in microbubble size was observed. Increase of the temperature to 25° C. led to strong microbubble growth, with about 81% of the microbubbles having sizes in the range 15–80 μm. Further temperature increase led to microbubble growth to sizes beyond the measuring range of the instrument.

Mixing of the perfluorobutane gas dispersion and 2-methylbutane emulsion at 37° C. led to rapid microbubble growth; after one 30 second measuring cycle 97% of the microbubbles had sizes in the range 15–80 μm.

b) Measurements Using Coulter Multisizer

Microbubble growth and the change in size distribution following mixture with diffusible component were analysed using a Coulter Multisizer II fitted with a 50 μm aperture and having a measuring range of 1–30 μm. The two components of each sample were added to the sample cell, which contained 200 ml Isoton II preheated to 37° C., at which temperature the measurements were performed. The size distribution of the mixture was measured immediately and 1.5 minutes after introduction of the samples. Thereafter the sample cell was exposed to ultrasound for 1 minute, using a 2.25 MHz transducer connected to a pulse generator; the energy level was 100 μJ.

b)(i) Mixing of the perfluorobutane gas dispersion from Example 1(ag) and perfluoropentane emulsion from Example 1(l) led to rapid and substantial microbubble growth after exposure to ultrasound. The total volume concentration increased from 3% to approximately 16%.

b)(ii) Mixing of the perfluorobutane gas dispersion from Example 1(ag) and perfluorobutane emulsion from Example 1(m) led to rapid and substantial microbubble growth. The total volume concentration increased from 1% to approximately 6%.

b)(iii) Mixing of the perfluorobutane gas dispersion from Example 1(ag) and perfluoropentane emulsion from Example 1(p) led to rapid and substantial microbubble growth after exposure to ultrasound. The total volume concentration increased from approximately 1% to approximately 4%.

b)(iv) Mixing of the perfluorobutane gas dispersion from Example 1(ag) and perfluoropentane emulsion from Example 1(af) led to rapid and substantial microbubble growth after exposure to ultrasound. The total volume concentration increased from approximately 2% to approximately 8%.

b)(v) Mixing of the perfluorobutane gas dispersion from Example 1(ag) and perfluoropentane/perfluoro-4-methylpent-2-ene emulsion from Example 1(q) led to rapid and substantial microbubble growth after exposure to ultrasound. The total volume concentration increased from 2% to approximately 4%.

b)(vi) Mixing of the perfluorobutane gas dispersion from Example 1(ag) and perfluoropentane/1H,1H,2-H-heptafluoropent-1-ene emulsion from Example 1(r) led to rapid and substantial microbubble growth. The total volume concentration increased from 2% to approximately 4.5%.

b)(vii) Mixing of the perfluorobutane gas dispersion from Example 1(ag) and perfluoropentane emulsion from Example 1(s) led to rapid and substantial microbubble growth after exposure to ultrasound. The total volume concentration increased from 2% to approximately 13%.

b)(viii) Mixing of the perfluorobutane gas dispersion from Example 1(ag) and perfluoropentane emulsion from Example 1(t) led to rapid and substantial microbubble growth after exposure to ultrasound. The total volume concentration increased from 2% to approximately 13%.

b)(ix) Mixing of the perfluorobutane gas dispersion from Example 1(ag) and perfluoropentane emulsion from Example 1(u) led to rapid and substantial microbubble growth after exposure to ultrasound. The total volume concentration increased from 3% to approximately 15%.

b)(x) Mixing of the perfluorobutane gas dispersion from Example 1(ag) and Perfluoropentane emulsion from Example 1(v) led to rapid and substantial microbubble growth after exposure to ultrasound. Tie total volume concentration increased from 3% to approximately 22%.

b)(xi). Mixing of the perfluorobutane gas dispersion from Example 1(ag) and perfluoropentane emulsion from Example 1(ai) led to rapid and substantial microbubble growth after exposure to ultrasound. The total volume concentration increased from approximately 3% to approximately 8%.

b)(xii) Mixing of the perfluorobutane gas dispersion from Example 1(ag) and perfluoropentane:perfluoro-4-methylpent-2-ene emulsion from Example 1(x) led to rapid and substantial microbubble growth after exposure to ultrasound. The total volume concentration increased from 2% to approximately 7.5%.

b)(xiii) Mixing of the perfluorobutane gas dispersion from Example 1(ag) and perfluoropentane:perfluoro-4-methylpent-2-ene emulsion from Example 1(y) led to rapid and substantial microbubble growth after exposure to ultrasound. The total volume concentration increased from 2.5% to approximately 7%.

b)(xiv) Mixing of the perfluorobutane gas dispersion from Example 1(ag) and perfluoropentane emulsion from Example 1(ac) led to rapid and substantial microbubble growth. The increase in the size of the microbubbles was more heavy and more rapid then that observed in Example 3(b)(xv). The total volume concentration increased from 3.5% to approximately 53%.

b)(xv) Mixing of the perfluorobutane gas dispersion from Example 1(ag) and perfluoropentane emulsion from Example 1(ae) led to rapid and substantial microbubble growth. The total volume concentration increased from 7% to approximately 19%. Exposure to ultrasound resulted in further microbubble growth indicated by an increase in the total volume concentration to approximately 54.5%.

b)(xvi) Mixing of the perfluoropropane gas dispersion from Example 1(ah) and perfluoropentane emulsion from Example 1(l) led to rapid microbubble growth, although not so heavy as observed in Example 3(b)(i). The total volume concentration increased from 3% to approximately 4.5%.

b)(xvii) Mixing of the perfluorobutane gas dispersion from Example 1(ag) and perfluoropentane emulsion from Example 1(o) led to rapid and substantial microbubble growth after exposure to ultrasound. The total volume concentration increased from approximately 1% to approximately 8%.

b)(xviii) A sample of perfluorohexane emulsion prepared as described in Example 1(ar) had a total concentration of droplets of 8.6 vol % and the droplet size was 2.6 μm.

b) (xix) A sample of 2,2,3,3,3-pentafluoropropyl methyl ether emulsion prepared as described in example 1(at) had a total concentration of droplets of 4.3 vol % and the droplet size was 1.5 μm.

b)(xx) A sample of 2H,3H-decafluoropentane emulsion prepared as described in Example 1(au) had a total concentration of droplets of 5.6 vol % and the droplet size was 1.9 μm.

b)(xxi) A sample of Perfluoroheptane emulsion prepared as described in Example 1(bj) had a total concentration of droplets of 8.5 vol % and the droplet size was 2.2 μm.

(c) Measurements Using Coulter Multisizer (140 μm Aperture)

Microbubble growth and change of size distribution following mixture with diffusible component emulsions were analysed using a Coulter Multisizer II fitted with a 140 μm aperture. The measuring range was set to 10–80 μm. The bubble dispersion and emulsion droplets were added to the sample cell containing 200 ml preheated Isoton II. The measurements were performed at 37° C. The size distribution of the mixture was measured immediately and 3 minutes after mixing. Thereafter the sample solution was exposed to ultrasound for 1 minute using a 2.25 MHz transducer connected to a pulse generator. The energy level was 100 μJ. The size distribution of the mixture was measured 1 minute and 3 minutes after exposure to ultrasound.

c)(i) Following addition of 182 μl of the heptafluoropent-1-ene emulsion prepared as described in Example 1(am) to 400 μl of a perfluorobutane gas dispersion prepared as described in Example 1(bl), the microbubbles immediately increased in size and the total volume concentration in the size range 10–80 μm was increased from insignificant to about 60 vol % within 1 minute.

c)(ii) Following addition of 70 μl of the perfluorodimethylcyclobutane emulsion prepared as described in Example 1(av) to 330 μl of perfluorobutane gas dispersion prepared as described in Example 1(bl), the microbubbles increased substantially in size after exposure to ultrasound. The total volume concentration in the size range 10–80 μm was increased from insignificant to about 14 vol % within 3 minutes.

c)(iii) Following addition of 71 μl of the perfluorodimethylcyclobutane emulsion prepared as described in Example 1(aw) to 330 μl of perfluorobutane gas dispersion prepared as described in Example 1(bl), the microbubbles increased substantially in size after exposure to ultrasound. The total volume concentration in the size range 10–80 μm was increased from insignificant to about 8.6 volt within 3 minutes.

c)(iv) Following addition of 105 μl of the perfluorodimethylcyclobutane emulsion prepared as described in Example 1(ax) to 300 μl of perfluorobutane gas dispersion prepared as described in Example 1(bl), the microbubbles increased in size after exposure to ultrasound. The total volume concentration in the size range 10–80 μm was increased from 3.2 volt to about 4.8 vol % within 3 minutes.

c)(v) Following addition of 105 μl of the perfluorodimethylcyclobutane emulsion prepared as described in Example 1(ay) to 300 μl of perfluorobutane gas dispersion prepared as described in Example 1(bl), the microbubbles increased in size after exposure to ultrasound. The total volume concentration in the size range 10–80 μm was increased from 1.5 vol % to about 2.2 vol % within 3 minutes.

c)(vi) Following redispersion of lyophilised perfluorobutane microbubbles in perfluorodimethylcyclobutane emulsion as described in Example 1(bg) an immediate increase in microbubble size occurred. The total volume concentration in the size range 10–80 μm was increased from insignificant to about 60 vol % within 1 minute.

c)(vii) Following addition of 76 μl of the 1-H-tridecafluorohexane emulsion prepared as described in Example 1(bi) to 400 μl of a perfluorobutane gas dispersion prepared as described in Example 1(bl), the microbubbles immediately increased in size and the total volume concentration in the size range 10–80 μm was increased from insignificant to about 20 vol % within 3 minures.

c)(viii) Following addition of 63 μl of the perfluorodimethylcyclobutane emulsion prepared as described in Example 1(bm) to 741 μl of a perfluorobutane gas dispersion prepared as described in Example 1(bl) the microbubbles immediately increased in size and the total volume concentration in the size range 10–80 μm was increased from insignificant to about 2 vol % within 3 minutes.

c)(ix) Following addition of 67 μl of the perfluorodimethylcyclobutane emulsion prepared as described in Example 1(aq) to 56 μl of perfluoropropane gas dispersion prepared as described in Example 1(bn) the microbubbles increased in size after exposure to ultrasound. The total volume concentration in the size range 10–80 μm was increased from insignificant to about 2.7 vol % within 1 minute.

EXAMPLE 4

In vitro Measurements of Acoustic Attenuation a) A sample of the perfluorobutane gas dispersion from Example 1(a) (1 μl) was suspended in Isoton II (55 ml) at 37° C. and acoustic attenuation was measured as a function of time using two broadband transducers with centre-frequencies of 3.5 MHz and 5.0 MHz in a pulse-echo technique. After 20 seconds a diffusible component was added to the suspension and measurements were continued for a further 120 seconds.

a)(i) Following addition of 100 μl of the 2-methylbutane emulsion from Example 1(c) attenuation immediately increased by a factor of more than 4; exact quantification was not possible since the attenuation exceeded the maximum value measurable by the system. The effect lasted for 50 seconds and was accompanied by a complete change in the shape of the attenuation spectra indicating a pronounced increase in microbubble size.

a)(ii) Addition of 20 μl of the 2-methylbutane emulsion from Example 1(c) led to a gradual increase in attenuation, reaching a maximum of between three and four times the initial value after 40 seconds and then decreasing rapidly. Again a complete change in the shape of the attenuation spectra indicated a pronounced increase in microbubble size.

a)(iii) Addition of 5 μl of the 2-methylbutane emulsion for Example 1(c) led to a gradual increase in attenuation, reaching a maximum of about 50% above the initial value after 30 seconds and then decreasing slowly towards the initial value. A shift towards lower resonance frequencies in the attenuation spectra indicated a moderate increase in microbubble size.

a)(iv) Addition of 500 µl of the 2-chloro-1,1,2-trifluoroethyl difluoromethyl ether emulsion from Example 1(e) led to a gradual increase in attenuation, reaching a maximum of about 50% above the initial value after 20 seconds and then decreasing slowly towards the initial value. A shift towards lower resonance frequencies in the attenuation spectra indicated a moderate increase in microbubble size.

a)(v) Addition of 500 µl of the perfluoropentane emulsion from Example 1(d) led to a small increase in attenuation. A shift towards lower resonance frequencies in the attenuation spectra indicated a small increase in microbubble size.

By way of control, addition of 500 µl of water produced no discernible change in attenuation.

b) A sample of the 2-methylbutane emulsion from Example 1(c) (100 µl) was added to the Isoton II (55 ml) at 37° C. and acoustic attenuation was measured as described in (a) above. After 20 seconds a sample of the perfluorobutane gas dispersion from Example 1(a) (1 µl) was added to the suspension and measurements were continued for a further 120 seconds. Attenuation increased rapidly following addition of the gas dispersion, reaching the maximum measuring level of the system after 20 seconds, and starting to decrease after 50 seconds. The attenuation spectra indicated the presence of large microbubbles.

By way of control, when 100 µl of water was used in place of the 2-methylbutane emulsion, attenuation increased rapidly following addition of the gas dispersion; after 40 seconds it reached a stable level one quarter of that measured using the 2-methylbutane emulsion. Attenuation remained at this level throughout the remainder of the 120 second measurement period. The attenuation spectra indicated the presence of small microbubbles.

EXAMPLE 5

In vivo Imaging of Dog Heart with Perfluorobutane Gas Dispersion [Comparative]

An injection syringe containing an amount of the perfluorobutane gas dispersion from Example 1(b) corresponding to 2 µl of gas content was prepared and the contents were injected into an open-chest 20 kg dog using a catheter inserted into an upper limb vein. Imaging of the heart was performed with a Vingmed CFM-750 scanner, using a midline short axis projection. The scanner was adjusted to acquire images once in each end-systole by gating to the ECG of the animal. Bright contrast was seen in the right ventricle a few seconds after the injection, and contrast of similar brightness appeared in the left ventricle some 4–5 seconds later, however with a substantial attenuation transiently hiding the posterior parts of the heart. Off-line digital backscatter intensity analysis was performed based on cineloop data recorded by the scanner. A brief, transient peak of contrast enhancement lasting some 10 seconds, beginning 3 seconds after the onset of contrast enhancement within the left ventricle was evident in a representative region of anterior left ventricle myocardium.

EXAMPLE 6

In vivo Imaging of Dog Heart with 2-methylbutane Emulsion [Comparative]

An injection syringe containing 1.0 ml of the 2-methylbutane emulsion from Example 1(c) was prepared and the contents were injected into the animal as in Example 5. Imaging of the heart was performed as described in Example 5. No contrast effects could be seen.

EXAMPLE 7

In vivo Imaging of Dog Heart with Perfluorobutane Gas Dispersion and 2-methylbutane Emulsion Injection syringes were prepared as in Examples 5 and 6 and the contents of both syringes were injected simultaneously into the dog via a Y-piece connector and the catheter described in Example 5. Imaging of the heart was performed as described in Example 5. The echo enhancement of the ventricles was similar to the observations in Example 5. In the left ventricular myocardium there was a monotonous rise in echo intensity in the 30 seconds following arrival of the contrast bolus to the coronary circulation. The contrast effects in the myocardium had completely vanished 5 minutes later.

EXAMPLE 8

In vivo Imaging of Dog Heart with Perfluoropentane Emulsion [Comparative]

An injection syringe containing 0.5 ml of the perfluoropentane emulsion from Example 1(d) was prepared and the contents were injected into the animal as in Example 5. Imaging of the heart was performed as described in Example 5. No signs of echo enhancement could be observed in any region of the image.

EXAMPLE 9

Low Intensity in vivo Imaging of Dog Heart with Perfluorobutane Gas Dispersion and Perfluoropentane Emulsion Injection syringes were prepared as in Examples 5 and 8 and the contents of both syringes were injected simultaneously into an open-chest 20 kg mongrel dog via a Y-piece connector and a catheter inserted into an upper limb vein. Imaging of the heart was performed with a Vingmed CFM-750 sanner, using a midline short axis projection. The scanner was adjusted to minimise acoustical output by lowering the emitted power to a value of 1 (on a scale ranging from 0 to 7), and by acquiring images only once in each end-systole by gating to the ECG of the animal. The observed contrast enhancement was as described in Example 5 with, however, a slightly prolonged duration in the myocardium.

EXAMPLE 10

High Intensity in vivo Imaging of Dog Heart with Perfluorobutane Gas Dispersion and Perfluoropentane Emulsion The experiment of Example 9 was repeated, except that the scanner output was adjusted to maximise ultrasound exposure to the imaged tissue region. This was done by using a combination of continuous high frame rate imaging and the highest output power (7 on a scale ranging from 0 to 7). After the injection, intense and bright contrast enhancement was seen in both ventricles of the heart. A steady rise in contrast enhancement was seen in all regions of the myocardium, up to an enhancement intensity approaching the maximum white level on the screen. The duration of tissue contrast was approximately 30 minutes, whilst contrast effects in the blood-pool declined to near baseline within 5 minutes of the injection, leaving an image with almost no blood-pool attenuation, and a complete and extremely bright circumferential contrast enhancement of the myocardium. The contrast effect in the myocardium close to the transducer did not seem to fade despite continuous high intensity ultrasound exposure.

EXAMPLE 11

High Intensity in vivo Imaging of Dog Heart with Perfluorobutane Gas Dispersion and Perfluoropentane Emulsion The procedure of Example 10 was repeated except that the perfluoropentane emulsion employed was prepared by cooling a solution of polyethylene glycol 10000 methyl ether 16-hexadecanoyloxyhexadecanoate (200 mg, prepared as in Example 2(k) of WO-A-9607434) in purified water (20 ml), transferring a 1 ml portion of this solution to a 2 ml vial, adding perfluoropentane (200 µl), shaking the vial for 45 seconds using a CapMix® and scoring the emulsion at 0° C. when not in use. The observed contrast enhancements of blood and myocardial tissue were as described in Example 5.

EXAMPLE 12

In vivo Imaging of Dog Kidney

The same substances and injection procedure as described in Example 9 were used. The left kidney of the dog was imaged through the intact abdominal wall using the same high output instrument settings as in Example 10. Central structures of the kidney containing the supplying arteries were included in the image. 20 seconds after the injection, the beginning of a steady rise in kidney parenchymal contrast enhancement was seen, reaching an intensity plateau of extreme brightness 1–2 minutes later. The transducer was moved to image the right kidney 4 minutes after the injection. At first, this kidney had a normal, non-enhanced appearance. However, this application of high intensity ultrasound was observed to generate a slight increase in echo intensity after a few minutes, although not up to the level that was observed in the left kidney.

EXAMPLE 13

In vivo Imaging of Dog Heart with Perfluorobutane Gas Dispersion and Reduced Amount of Perfluoropentane Emulsion The procedure of Example 10 was repeated except that the dose of the perfluoropentane emulsion was reduced to one third. The peak intensity of myocardial contrast enhancement was comparable to that observed in Example 10, but the duration of tissue contrast was reduced from 30 minutes to less than 10 minutes.

EXAMPLE 14

Closed-chest in vivo Imaging of Dog Heart with Perfluorobutane Gas Dispersion and Perfluoropentane Emulsion The procedure of Example 10 was repeated in a closed-chest experiment. The myocardial contrast enhancement was comparable to that observed in Example 10.

EXAMPLE 15

Colour Doppler in vivo Imaging of Dog Heart with Perfluorobutane Gas Dispersion and Perfluoropentane Emulsion The procedure of Example 10 was repeated except that the scanner (in the colour Doppler mode) was applied to the left heart ventricle during the first minute after injection in order to initiate microbubble growth. Thereafter the myocardial contrast enhancement was more intense than that observed in Example 10.

EXAMPLE 16

In vivo Imaging of Dog Heart with Perfluorobutane Gas Dispersion and perfluoro-4-methylpent-2-ene Emulsion 0.5 ml of isotonically reconstituted perfluorobutane gas dispersion prepared in accordance with Example 1(ag) and 66 µl of the perfluoro-4-methylpent-2-ene emulsion from Example 1(al) were injected as described in Example 10. The resulting myocardial contrast enhancement was comparable in intensity to that observed in Example 10, but had a duration of 6–8 minutes.

EXAMPLE 17

In vivo Imaging of Hyperemic Region of Dog Heart with Perfluorobutane Gas Dispersion and Perfluoropentane Emulsion A branch of the circumflex coronary artery of the dog was temporarily ligated for 2 minutes, whereafter contrast agent was injected as described in Example 10. Contrast enhancement of the now hyperaemic myocardium was substantially more intense than that of surrounding normal tissue.

EXAMPLE 18

In vivo Imaging of Dog Heart with Perfluorobutane Gas Dispersion and Perfluorodimethylcyclobutane Emulsion 0.5 ml of isotonically reconstituted perfluorobutane gas dispersion prepared in accordance with Example 1(ag) and 66 µl of the perfluorodimethylcyclobutane emulsion from Example 1(ao) were injected as described in Example 10. The resulting intense myocardial contrast enhancement was comparable to that observed in Example 16.

EXAMPLE 19

In vivo Imaging of Dog Heart with Perfluorobutane Gas Dispersion and Perfluorodimethylcyclobutane Emulsion 0.5 ml of isotonically reconstituted perfluorobutane gas dispersion prepared in accordance with Example 1(bl) and 66 µl of the perfluorodimethylcyclobutane emulsion from Example 1(aq) were injected as described in Example 10. The resulting intense myocardial contrast enhancement was comparable to that observed in Example 16.

EXAMPLE 20

In vivo "Particle-to-particle" Targeting 0.02 µl/kg of biotinylated perfluorobutane microbubbles prepared according to Example 1(bq), and 0.02 µl/kg of perfluorodimethylcyclobutane emulsion prepared as described in Example 1(bh) are simultaneously intravenously injected into a 20 kg anaesthetised mongrel dog, while the heart is imaged by ultrasound as described in Example 10. Myocardial echo enhencement was similar to that observed in Example 10, except that the peak of attenuation in the left ventriclar blood was far less pronounced.

EXAMPLE 21

In vivo Imaging of Rabbit Heart with Perfluorobutane Gas Dispersion and Perfluorodimethylcyclobutane Emulsion An injection syringe containing an amount of the perfluorobutane microbubble dispersion prepared as in Example 1(bl) (volume median diameter 3.0 μm) corresponding to 1 μl of gas content and a further injection syringe containing 105 μl of the perfluorodimethylcyclobutane emulsion from Example 1(aq) were prepared. The contents of both syringes were injected simultaneously into a 5 kg rabbit using a catheter inserted into an ear vein. B-mode imaging of the heart was performed using an ATL HDI-3000 scanner with a P5-3 probe, using an open thorax parasternal short axis projection. The results were comparable to those observed in Example 18.

EXAMPLE 22

Ultrasonication-induced Drug Delivery

A 3 kg anaesthetised New Zealand Black rabbit was injected intravenously with 0.04 ml of perfluorodimethylcyclobutane emulsion prepared as described in Example 1(aq) and simultaneously with 0.12 ml of perfluorobutane gas suspension prepared as described in Example 1(bl), while the left kidney was imaged with an ATL HDI-3000 scanner with a P5-3 probe, the scanner being adjusted for maximum output power. Significant bubble growth and accumulation within the kidney parenchyma was observed. Then 160 mg of FITC-dextran (mw 2,000,000) was dissolved in 5 ml of water and injected intravenously, and ultrasound imaging at the same site was continued for another 5 minutes, now swithcing the scanner to Power Doppler mode to maximise acoustical output. The animal was then sacrificed, and both kidneys were removed and examined in ultraviolet light. An increased amount of fluorescence was observed as 50–100 μm spots in the interstitium within the regions of the left kidney that were exposed to imaging ultrasound in the presence of microbubbles. Associated with each such spot was a nephron devoid of intravascular fluorescence.

EXAMPLE 23

Albunex® as Gas Dispersion 0.3 ml/kg of Albunex® and 1.5 μl/kg of perfluorodimethylcyclobutane emulsion prepared as described in Example 1(aq) were injected intravenously into a 20 kg anaesthetised male mongrel dog and imaged by ultrasound as described in Example 10. The myocardial enhancement was as described in Example 10.

EXAMPLE 24

Targeted Microbubbles in Imaging of Rabbit Heart 0.1 μl/kg of microbubbles prepared as described in Example 1(az) were injected intravenously into a rabbit, while imaging the rabbit's heart by ultrasound using an ATL HDI-3000 scanner with a P5-3 probe. A faint but lasting myocardial echo enhancement was seen. Three minutes later, 1.5 μl/kg of perfluorodimethylcyclobutane emulsion prepared as described in Example 1(aq) was injected. A slight increase in the echo intensity from the insonified myocardium was observed.

EXAMPLE 25

In vivo Imaging of Rat Heart with Perfluorobutane Gas Dispersion and Perfluorodimethylcyclobutane Emulsion The experiment described in Example 19 was performed on a rat, with comparable results.

EXAMPLE 26

In vivo Imaging of Dog Heart with Perfluorobutane Gas Dispersion and Perfluorohexane Emulsion 0.1 μl/kg of perfluorohexane emulsion prepared as described in Example 1(ar) and 0.2 μl/kg of the perfluorobutane microbubble suspension prepared as decribed in Example 1(bl) were injected simultaneously into a dog as described in Example 10. The myocardial contrast effect was comparable to that observed in Example 10.

EXAMPLE 27

In vivo Imaging of Dog Heart with Perfluorobutane Gas Dispersion and heptafluoropent-1-ene Emulsion 0.3 μl/kg of the perfluorobutane microbubble suspension prepared as described in Example 1(bl) and 0.15 ml of the heptafluoropent-1-ene emulsion described in Example 1(am) were injected simultaneously into a dog as described in Example 10. A relatively weak myocardial contrast effect was observed, which was however more intense and more long-lasting than that which was observed in Example 5.

EXAMPLE 28

In vivo Imaging of Dog Heart with Perfluorobutane Gas Dispersion and Perfluorodimethylcyclobutane Emulsion Stabilised with Sterilised Phospholipid 0.3 μl/kg of a perfluorobutane microbubble suspension prepared as described in Example 1(bl) and 0.3 μl/kg of the perfluorodimethylcyclobutane emulsion prepared as described in Example 1(bm) were injected simultaneously into a dog as described in Example 19. A myocardial contrast effect comparable to that described in Example 19 was observed.

EXAMPLE 29

In vivo Imaging of Dog Heart with Perfluoropropane Gas Dispersion and Perfluorodimethylcyclobutane Emulsion 0.17 ml of the perfluoropropane microbubble suspension prepared as described in Example 1(bn) and 0.3 μl/kg of the perfluorodimethylcyclobutane emulsion prepared as described in Example 1(aq) were injected simultaneously into a dog as described in Example 19. A myocardial contrast effect comparable to that described in Example 19 was observed.

EXAMPLE 30

In vivo Imaging of Dog Gastrointestinal Tract with Perfluorobutane Gas Dispersion and Perfluorodimethylcyclobutane Emulsion 20 ml of an emulsion of perfluorodimethylcyclobutane, prepared as described in Example 1(aq) is given via a gastric tube to an anaesthetised dog. Thereafter a small amount (dose range 0.1–0.2 μl gas/kg) of a perfluorobutane microbubble dispersion prepared as in Example 1(a) is injected intravenously. An ultrasound imaging transducer is applied onto the abdominal wall, and localised microbubble growth in the gastric wall capillary system provides enhanced contrast with improved delineation of the mucosal contours.

EXAMPLE 31

In vivo imaging of Dog Gastrointestinal Tract with Perfluorobutane Gas Dispersion and Perfluorodimethylcyclobutane Emulsion A perfluorobutane microbubble dispersion prepared as in Example 1(a) is given via a gastric tube to an anaesthetised dog. The dispersion is allowed to distribute evenly inside the gastric ventricle, as verified by ultrasound imaging. A small amount of an emulsion of perfluorodimethylcyclobutane, prepared as described in Example 1(aq)(dose range 0.2–1 µl perfluorocarbon/kg), is injected intravenously. The ultrasound transducer is maintained on the region of interest; microbubble growth in the gastric fluid layers proximal to the mucosal surfaces provides enhanced contrast with improved delineation of the mucosal contours.

EXAMPLE 32

In vivo Imaging of Dog Heart with Perfluorobutane Gas Dispersion and Perfluorodimethylcyclobutane Emulsion and Coadministered Adenosine An occluding snare was placed around a major branch of the left anterior descending coronary artery of an open-chest 22 kg dog and an ultrasound transit time flowmeter was placed immediately downstream of the occluder, which was then adjusted to produce a steady 25% flow reduction from about 14 to 10 ml/min. The contents of three syringes, respectively containing (i) an amount of a perfluorobutane microbubble dispersion prepared as in Example 1(bl) corresponding to 4.4 µl of gas content, (ii) an amount of the perfluorodimethylcyclobutane emulsion from Example 1(aq) corresponding to 33 µl of the dispersed perfluorodimethylcyclobutane phase, and (iii) 3.0 mg adenosine dissolved in 0.9% saline, were then intravenously injected as a simultaneous bolus; commencing 10 seconds later a further 3.0 mg of adenosine dissolved in 0.9% saline was injected slowly over 20 seconds. Imaging of the left ventricle of the heart was performed using an ATL HDI-3000 scanner with a P5-3 probe; continuous ultrasonication at maximum power was applied for 1 minute to induce microbubble growth, whereafter the myocardium was examined using B-mode imaging. A clearly evident difference in gray scale levels could be seen between stenotic areas (brighter than baseline recordings) and normal areas (very much brighter than baseline recordings).

What is claimed is:

1. A combined preparation for simultaneous, separate or sequential use as a deposit perfusion tracer contrast agent in ultrasound imaging, said preparation comprising:
    i) an injectable aqueous medium having gas dispersed therein; and
    ii) a composition comprising a diffusible component, said diffusible component being separate from said dispersed gas and being capable following administration of the combined preparation to a human or non-human animal subject, of diffusion in vivo into said dispersed gas so as to promote controllable growth and temporary retention of said dispersed gas within tissue microvasculature in said subject.

2. A combined preparation as claimed in claim 1 wherein the dispersed gas is selected from the group consisting of air, nitrogen, oxygen, carbon dioxide, hydrogen, inert gases, sulphur fluorides, selenium hexafluroride, optionally halogenated silanes, low molecular weight hydrocarbons, ketones, esters, halogenated low molecular weight hydrocarbons and mixtures of any of the foregoing.

3. A combined preparation as claimed in claim 2 wherein the gas is selected from the group consisting of perfluorinated ketones, perfluorinated ethers and perfluorocarbons.

4. A combined preparation as claimed in claim 3 wherein the perfluorocarbon is selected from the group consisting of perfluoroalkanes, perfluoroalkenes and perfluorocycloalkanes.

5. A combined preparation as claimed in claim 2 wherein the gas is selected from the group consisting of sulphur hexafluoride, perfluoropropane, perfluorobutanes and perfluoropentanes.

6. A combined preparation as claimed in claim 1 wherein the dispersed gas is stabilised by a coalescence-resistant surface membrane, a filmogenic protein, a polymer material, a non-polymeric and non-polymerisable wall-forming material or a film-forming surfactant material.

7. A combined preparation as claimed in claim 6 wherein said film-forming surfactant material comprises at least one phospholipid.

8. A combined preparation as claimed in claim 7 wherein at least 75% of the said film-forming surfactant material comprises phospholipid molecules individually bearing net overall charge.

9. A combined preparation as claimed in claim 8 wherein at least 75% of the film-forming surfactant material comprises one or more phospholipids selected from phosphatidylserines, phosphatidylglycerols, phosphatidylinositols, phosphatidic acids and cardiolipins.

10. A combined preparation as claimed in claim 9 wherein at least 80% of said phospholipids comprise phosphatidylserines.

11. A combined preparation as claimed in claim 1 wherein the composition comprising the diffusible component is formulated for administration cutaneously, subcutaneously, intramuscularly, intravenously or by inhalation.

12. A combined preparation as claimed in claim 1 wherein the composition comprising the diffusible component further comprises a carrier liquid.

13. A combined preparation as claimed in claim 12 wherein the diffusible component is dispersed in an aqueous carrier liquid in the form of an oil-in-water emulsion or microemulsion.

14. A combined preparation as claimed in claim 13 wherein the diffusible component is selected from the group consisting of aliphatic ethers, polycyclic oils, polycyclic alcohols, heterocyclic compounds, aliphatic hydrocarbons, cycloaliphatic hydrocarbons, and halogenated low molecular weight hydrocarbons.

15. A combined preparation as claimed in claim 14 wherein the diffusible component comprises a perfluorocarbon.

16. A combined preparation as claimed in claim 15 wherein the perfluorocarbon is selected from the group consisting of perfluoroalkanes, perfluoroalkenes, perfluorocycloalkanes, perfluorocycloalkenes, and perfluorinated alcohols.

17. A combined preparation as claimed in claim 16 wherein the diffusible component is selected from the group consisting of perfluoropentanes, perfluorohexanes, perfluorodimethylcyclobutanes and perfluoromethylcyclopentanes.

18. A combined preparation as claimed in claim 13 wherein the emulsion is stabilised by a phospholipid surfactant.

19. A combined preparation as claimed in claim 18 wherein at least 75% of the said phospholipid surfactant comprises molecules individually bearing net overall charge.

20. A combined preparation as claimed in claim 19 wherein at least 75% of the phospholipid surfactant is selected from phosphatidylserines, phosphatidylglycerols, phosphatidylinositols, phosphatidic acids and cardiolipins.

21. A combined preparation as claimed in claim 20 wherein at least 80% of said phospholipid surfactant comprises phosphatidylserines.

22. A combined preparation as claimed in claim 1 which further includes a therapeutic agent.

23. A combined preparation as claimed in claim 1 which further includes contrast-enhancing moieties for an imaging modality other than ultrasound.

24. A method of generating enhanced images of a human or non-human animal subject which comprises the steps of:
   i) injecting a physiologically acceptable aqueous medium having gas dispersed therein into the vascular system of said subject;
   ii) before, during or after injection of said aqueous medium administering to said subject a composition comprising a diffusible component capable of diffusion in vivo into said dispersed gas so as to promote controllable growth and temporary retention of said dispersed gas within tissue microvasculature in said subject; and
   iii) generating an ultrasound image of at least a part of said subject.

25. A method as claimed in claim 24 wherein the composition comprising the diffusible component is administered cutaneously, subcutaneously, intramuscularly, intravenously or by inhalation.

26. A method as claimed in claim 24 wherein a vasodilator drug is coadministered to the subject.

27. A method as claimed in claim 26 wherein said vasodilator drug is adenosine.

28. A method as claimed in claim 24 wherein preliminary localised ultrasound is applied to induce said increase in size of the dispersed gas.

29. A method as claimed in claim 28 wherein colour Doppler imaging ultrasound is employed as said preliminary localised ultrasound.

30. A combined preparation as claimed in claim 1 which further includes a vasodilator drug.

31. A combined preparation as claimed in claim 30 wherein said vasodilator drug is adenosine.

32. A combined preparation for simultaneous, separate or sequential administration use as a deposit perfusion tracer contrast agent in ultrasound imaging, said preparation comprising:
   i) an injectable aqueous medium having gas dispersed therein; and
   ii) an injectable oil-in-water emulsion or microemulsion in which the oil phase is separate from said dispersed gas and comprises a volatile liquid such that, following administration of the combined preparation to a human or non-human animal subject, molecules of gas or vapour from said volatile liquid diffuse in vivo into said dispersed gas so as to promote controllable growth and temporary retention of said dispersed gas within tissue microvasculature in said subject.

* * * * *